US011375990B2

(12) United States Patent
Price

(10) Patent No.: US 11,375,990 B2
(45) Date of Patent: Jul. 5, 2022

(54) CARDIAC ATRIAL RETRACTOR RING

(71) Applicant: Bobby S. Price, Marietta, GA (US)

(72) Inventor: Bobby S. Price, Marietta, GA (US)

( * ) Notice: Subject to any disclaimer, the term of this patent is extended or adjusted under 35 U.S.C. 154(b) by 21 days.

(21) Appl. No.: 17/052,754

(22) PCT Filed: May 3, 2019

(86) PCT No.: PCT/US2019/030678
§ 371 (c)(1),
(2) Date: Nov. 3, 2020

(87) PCT Pub. No.: WO2019/213582
PCT Pub. Date: Nov. 7, 2019

(65) Prior Publication Data
US 2021/0236108 A1    Aug. 5, 2021

Related U.S. Application Data

(60) Provisional application No. 62/666,209, filed on May 3, 2018.

(51) Int. Cl.
*A61B 17/02* (2006.01)

(52) U.S. Cl.
CPC .. *A61B 17/0218* (2013.01); *A61B 2017/0237* (2013.01); *A61B 2017/0287* (2013.01)

(58) Field of Classification Search
CPC ........ A61B 17/0218; A61B 2017/0237; A61B 2017/0287; A61F 2/2409; A61F 2/445; A61F 2/2412
USPC ................................................ 600/201–245
See application file for complete search history.

(56) References Cited

U.S. PATENT DOCUMENTS

| | | | | |
|---|---|---|---|---|
| 5,258,021 A | * | 11/1993 | Duran | A61F 2/2412 623/2.36 |
| 5,613,937 A | | 3/1997 | Garrison et al. | |
| 8,512,403 B2 | | 8/2013 | Navia et al. | |
| 9,526,615 B2 | | 12/2016 | Carpentier et al. | |
| 2007/0225801 A1 | * | 9/2007 | Drews | A61F 2/2412 623/2.11 |
| 2011/0137128 A1 | | 6/2011 | Poo et al. | |

(Continued)

FOREIGN PATENT DOCUMENTS

DE   202011101601 U1   12/2011
WO      2017196912 A1   11/2017

OTHER PUBLICATIONS

Renteria et al. "Striated Membranous Structures in Human Hearts". American Journal of Pathology. <https://www.ncbi.nlm.nih.gov/pmc/articles/pmc2032552/>. vol. 85, Issue 1, pp. 85-98. Oct. 1976.

(Continued)

*Primary Examiner* — Eduardo C Robert
*Assistant Examiner* — Tara Rose E Carter
(74) *Attorney, Agent, or Firm* — Perilla Knox & Hildebrandt LLP

(57) ABSTRACT

Disclosed are various embodiments for an atrial retractor designed to expose the valves of the heart. The device is made in the shape of an interrupted ring with inset legs to reach into the atria. Segments of the ring, legs, and feet may be made of an elastic material to provide force for retraction of tissue to allow the workspace to be accessible for any surgical procedure to the valves.

20 Claims, 44 Drawing Sheets

(56) References Cited

U.S. PATENT DOCUMENTS

2015/0216658 A1* 8/2015 Braido ................. A61F 2/2433
623/2.13

OTHER PUBLICATIONS

International Search Report and Written Opinion for International Application No. PCT/US19/30678 dated Jul. 17, 2019.

* cited by examiner

8

CARDIAC ATRIAL RETRACTOR RING

CROSS-REFERENCE TO RELATED APPLICATION

This application is a 35 U.S.C. § 371 national stage application of International Application No. PCT/US2019/030678, filed on 3 May 2019, which claims priority to and the benefit of, U.S. Provisional Application No. 62/666,209, filed on 3 May 2018, herein incorporated by reference in its entirety.

BACKGROUND

Current surgical practices can repair or replace a damaged valve in a human heart. One difficulty in this procedure is accessing the valve in its central position within the heart. Not only is the surgeon working inside the thoracic cavity of the patient, but they also must work within the confines of the heart itself.

SUMMARY OF INVENTION

Described herein are cardiac atrial retractor rings and methods relating to atrial retraction of a heart.

In an embodiment according to the present disclosure, a cardiac atrial retractor ring is described that is operable to be flexed between a compressed position having a first circumference and an expanded position having a second circumference, the first circumference being smaller than the second circumference.

In embodiments according to the present disclosure, cardiac atrial retractor rings as described herein can further comprise a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment.

In embodiments according to the present disclosure, cardiac atrial retractor rings as described herein can further comprise a plurality of traction points extending outwardly from the plurality of annular segments away from the central point.

In embodiments of the present disclosure, an interference between corresponding flexing members of cardiac atrial retractor rings as described herein can prevent the corresponding flexing member from being flexed fully inwardly to the plane.

In embodiments of the present disclosure, the corresponding flexing member of cardiac retractor rings as described herein can include a pair of legs that extend away from the plane when the corresponding flexing member is flexed outwardly away from the central point when the cardiac atrial retractor ring is in the expanded position, and the pair of legs is joined by a foot.

In embodiments of the present disclosure, cardiac retractor rings as described herein can further comprise a respective traction point extending outwardly from each leg of the pair of legs away from the central point.

In embodiments of the present disclosure, cardiac retractor rings as described herein can have a distance between the pair of legs is reduced when the corresponding flexing member flexes inwardly toward the central point and increased when the corresponding flexing member flexes outwardly away from the central point.

In embodiments of the present disclosure, the pair of legs of cardiac retractor rings as described herein can be inset toward the central point from the respective annular segment and the adjacent annular segment.

In embodiments of the present disclosure, the foot of cardiac retractor rings as described herein can be of a different shape in cross-section than the pair of legs.

In embodiments of the present disclosure, the foot of cardiac retractor rings as described herein can comprise an arch that varies in height but not length to move the pair of legs.

In embodiments of the present disclosure, an entirety of the cardiac atrial retractor ring can be formed from a continuous length of a memory metal wire.

In embodiments of the present disclosure, an entirety of the cardiac atrial retractor ring can be formed from a continuous length of an elastic plastic material.

In embodiments of the present disclosure, a diameter of the cardiac atrial retractor ring can be between 20 millimeters and 80 millimeters.

In embodiments of the present disclosure, a change between the compressed position and the expanded position of cardiac atrial retractor rings as described herein can be thermally actuated.

Methods relating to atrial retraction of a heart also described herein. According to an embodiment of the present disclosure, a method for retracting an atrium of a heart, can comprise: inserting a cardiac atrial retractor ring according to the present disclosure into the atrium when the cardiac atrial retractor ring is in a compressed position, wherein the cardiac atrial retractor ring is operable to be flexed between the compressed position having a first circumference and an expanded position having a second circumference, the first circumference being smaller than the second circumference; and expanding the cardiac atrial retractor ring into the expanded position, thereby retracting the atrium. According to embodiments of methods of the present disclosure, the cardiac atrial retractor ring can be inserted through a laparoscopic port. According to embodiments of methods of the present disclosure, the cardiac atrial retractor ring can expand into the expanded position in response to a change in temperature.

Methods as described herein can further comprise engaging striated fibril tissue of the atrium with a plurality of traction points surrounding a cardiac atrial retractor ring according to the present disclosure.

Methods as described herein can further comprise compressing a cardiac atrial retractor ring as described herein from the expanded position to the compressed position.

According to methods of the present disclosure, a cardiac atrial retractor ring can comprise a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
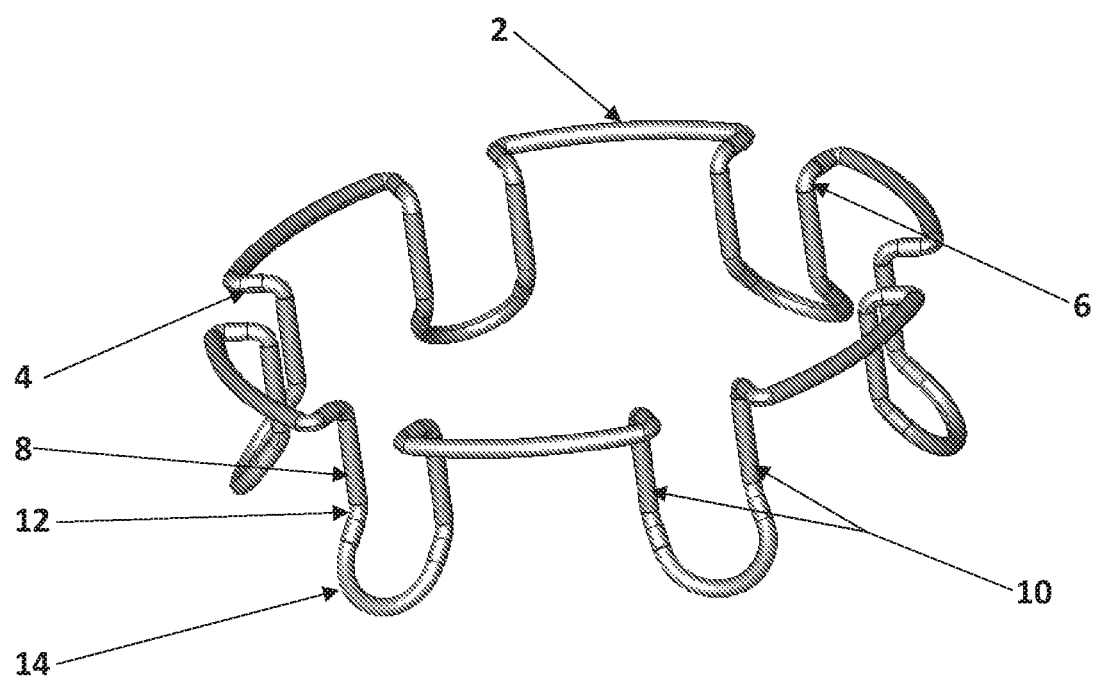
FIG. 1 shows an embodiment of a cardiac atrial retractor ring constructed in a round material format.

The present disclosure relates to an atrial retractor designed to expose the valves of the heart. This cardiac atrial retractor ring is operable to be flexed between a compressed position having a first circumference and an expanded position having a second circumference. An objective of this device is to work with traditional surgical approaches to provide an easier method of exposing a valve. As a result, the time that the patient is on cardiac bypass and anesthesia can be reduced. Many patients who require this type of procedure are at risk the longer they are on such support processes, so a decrease in surgical time can lead to better postsurgical outcomes. Faster times can also relieve stress on the surgical staff who perform these procedures.

The device is made in the shape of an interrupted ring with inset legs to reach into the atria. In particular, the cardiac atrial retractor ring comprises a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment. The flexing member may be said to comprise members that are insets, legs, knees, and feet as described herein.

Segments of the ring, legs, and feet are made of an elastic material to provide force for retraction of tissue to allow the workspace to be accessible for any surgical procedure to the valves. An embodiment includes a base ring at the top that is large enough to keep the device from fitting into the atrial annulus. A diameter for this could range from 20 mm to 80 mm depending on the size of the heart. This ring may sit on top of the atrial appendage or be enveloped just underneath its tissue. The ring may be segmented with open spaces containing inward bends to inset the legs by an amount necessary for the size of the atrial opening. These insets could vary in length from 2 mm to 20 mm to achieve the proper leg position.

The top of the legs are inset to the point that the deployed device will spread open the tissue of the atria for a good view of the atrial workspace. The diameter of this opening could vary from 20 mm to 60 mm depending on the size of the heart. The inward ends of the base ring insets and the top of the legs may meet at a knee; a knee being a flexible and elastic junction to allow the legs to rotate about the knee cross-axis applying the proper force to the atrial wall for retraction.

The leg may start at the bottom of the knee and extend vertically down to a shallow bend outward at its bottom end called an ankle. The leg would be long enough to reach into the atria to the bottom of the ostium. This could involve leg lengths between 5 mm and 30 mm. A slight bend outward at the bottom of the leg, the ankle, may allow the foot to seat itself in the atrial wall.

The feet may be located at the bottom end of the legs, attaching two legs into a pair that work together. Each foot may be made of a horizontal strut of flexible and elastic material formed into an arch that may change in height, but not length, to move its pair of legs closer together or further apart. An approximate chord length for each foot would fall between 4 mm and 10 mm depending on the strength of the material used and the desired change in chord length. The apex of the arch should be oriented so that when the foot contracts it does not interfere with the atrial tissue. This is simply achieved by having the arch run on the same axis as the leg.

In various embodiments, the entire device is constructed out of a single piece of medical grade material such as elastic shape memory metal wire like a nickel/titanium alloy or possibly a strong but elastic plastic. This allows the entire device to be deformable for insertion through a laparoscopic port if it is to be used in such surgery. This may also make manufacturing of the device simpler and quicker. If metal wire is used, a wire diameter of between 0.5 mm and 3 mm may be enough to give the proper rigidness for use while allowing for the flexibility that would be required.

Various embodiments incorporate medically safe stainless-steel wire body sections for all non-articulating sections. This produces more rigidity to the framework of the device as to produce the required geometry for its intended usage if required. The articulated sections of the device, including the feet and knees, could be made of a shape memory metal, such as a nickel/titanium alloy, to give the flexibility and force required for retraction of the atrial tissue.

In one embodiment, the arch of the feet could be flipped upward relative to the legs. This embodiment would produce smaller contact points from the bottom end of the legs to possibly achieve better traction with the striated fibril formations of the tissue below the ostium. The inverse arch would also allow a higher arch to be used which would increase the amount that the ring could expand in diameter. This could be favorable as it may allow for easier insertion of the device during its placement and a wider field of view of the work environment for the surgical procedure.

Another embodiment adds traction points to the outer diameter of the base ring. For example, the cardiac atrial retractor ring may have a plurality of traction points extending outwardly from the plurality of annular segments away from the central point. These would be used to hold the ring solidly in place while it is seated in the fold of the atrial appendage tissue. These formations would not need to be aggressive. They only need to be designed to seat properly in the striated fibril tissue of the inside of the atrial appendage. These points could include any number of individual conical or parabolic tines spaced around the base ring's circumference and extending between 1 mm and 3 mm from the base ring, or areas of low-profile knurling along the surface of each base ring segment.

Another embodiment incorporates elastic arches around the base ring or at the top of the leg pairs, designed similarly to the feet. These could be situated around the circumference of the base ring, in between the legs, and oriented in a horizontal position with the arch peaks pointed towards the center or down so as not to interfere with the outer contact surface area of the ring in the event it is used in the fold of the atrial appendage.

Any of these embodiments could be used or not in conjunction with each other as needed. They would not interfere with each other if employed. Their use is meant only to augment the device to fulfill its intended purpose.

The design goals of this project are achieved by its simple and intuitive use for retracting the atria of the heart. While flexible and elastic, the design may have no mechanical moving parts. The articulating features of the design bend into place, possibly on a change in temperature if memory metal is used, in order to form a framework structure to hold open the atrial chamber while the elastic nature of the device expands its dimensions to retract the tissue to achieve the open workspace required to perform the surgical procedure as necessary.

Once the heart is exposed through the preferred method and a standard incision is made in the atrial appendage, the device is brought to the opening of the atria, possibly in its closed state. This closed state is achieved by the contraction of the flexible and elastic material of the feet, and possibly the base ring, into their high arch positions. These arches, when contracted would pull the leg pairs together to shrink the diameter of the annular shape to a suitable size, relative to the atrial opening, to allow the diameter of the ring of legs to fit easily into the atria.

Also, the elastic knees at the top of each leg would be extended, rotating all the leg up and towards the center of the ring. This would form a semi-conical shape with the legs and feet for ease of inserting and centering the ring in the opening of the atria. These articulating pieces of the device could be made of a thermally reactive shape memory metal, like a nickel/titanium alloy, that could be cooled to produce this contracted state, but would then warm to the body temperature after insertion to bend to their relaxed state.

As the device is warmed by the surrounding tissue, the articulations could expand to a second state securing itself in place and retracting the tissue. The legs would fold down into the heart and come to rest against the walls of the atria. This would position the feet just below the smooth tissue of the ostium into the striated fibril tissue surrounding the valve, but they should leave enough space below themselves for surgical work to be accomplished without interference. The contact point of the feet against the atrial wall at this point would hold the device from sliding free of the heart by not easily pulling up over the boundary of the ostium tissue. Force from the knees and the expanding diameter of the ring would apply sufficient force to make this secure.

If a more secure seating is desired, it could be possible to use the base ring to assist by wrapping the incised atrial appendage tissue over top of the device. The base ring in its extended diameter would be larger than the opening in the atria, but the tissue of the atrial appendage is highly elastic and should be able to completely envelop the base ring. This could be made to be highly secure by the addition of small non-traumatic protrusions to the outer diameter of the ring material. These protrusions could be made to a scale that would add traction to the striated fibril inner lining of the atrial appendage. With the proper extended diameter of the base ring and the addition of protrusions to its outer surface, the device would be very secure in its seating when positioned properly. This may take slightly longer to deploy in this fashion, but if there were less issues with its fit during a procedure, this could be acceptable.

While the legs are folding down to position the feet, the temperature change would also cause the feet themselves to expand. This would cause the pairs of leg struts to spread apart causing an increase in circumference and thereby diameter of the device. The tissue of the atria would be retracted and spread in this way by the legs being pushing outward. This would create more space to work for the surgeon and keep the view clear.

The force that is necessary to perform as needed would not be great, but if more force is needed than what can be provided by the material of the feet, or if the force needed to be distributed more evenly, extra expanding arches may be incorporated in various embodiments. These arches could be similar in design to the feet and could be positioned either further up on the legs or set in the openings in the base ring. These positions could add force to a higher location on the device. This could be used to even out the stress on the structure of the device if necessary, based on the requirements of the materials used for construction.

Removal of the device when work inside the heart is completed could be accomplished by cooling the device to contract the articulating components if such capability is available. Otherwise a careful manipulation and pull on the device should be sufficient to extract it without damage to the heart tissue. It will be seated, but if the base ring is free from the appendage, the flexibility of the knees should allow the feet to slowly be slid over the atrial tissue for removal. The heart tissue should be resilient and flexible enough to do this without damage.

FIG. 1 shows an embodiment constructed in a round material format. This model can function as a base layout for all models listed in this description. As such, the features described here will be seen in further figures but will only be described here. The overall shape of the device is annular. The top of the device comprises the base ring which is made in six segments (2). Each end of the base ring segments curves inward to create an inset (4) for the rest of the design. The form then curves downward. This curvature forms the knees (6). The form continues down from the knees forming the legs (8), which come in pairs (10) that are formed by the legs of adjacent base ring segments. The pairs of legs extend away from the plane when the corresponding flexing member is flexed outwardly away from the central point when the cardiac atrial retractor ring is in the expanded position. The lower end of each leg may contain an outward curvature referred to as the ankle (12). Each of the six pairs of legs are connected at the bottom by a foot (14) that spans the distance between the legs.

Figure 2:
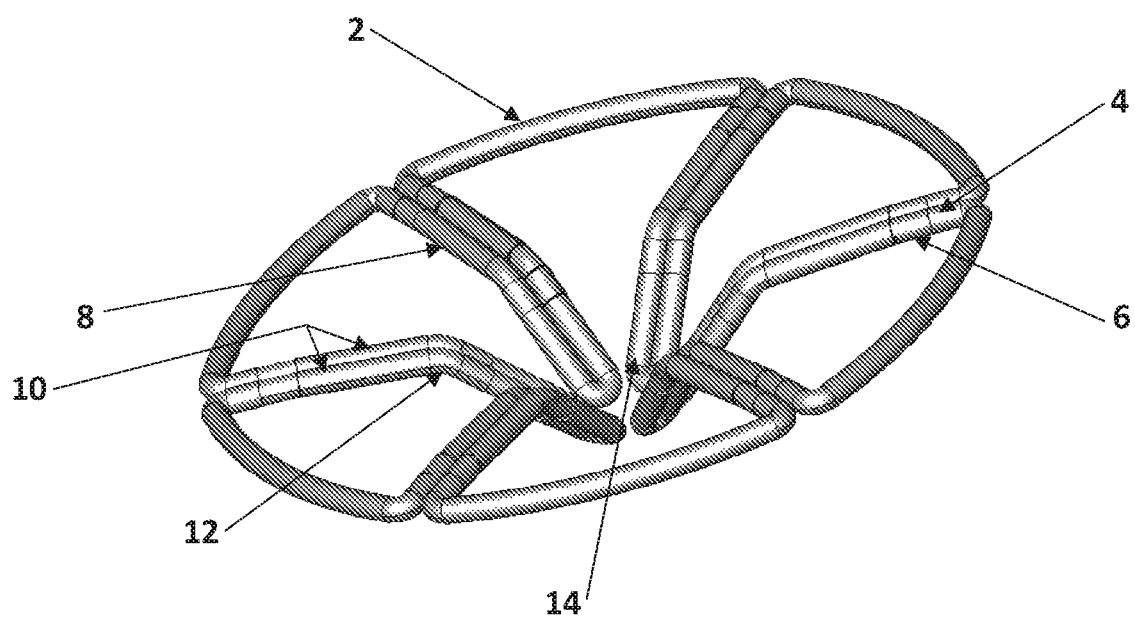
FIG. 2 shows the embodiment of FIG. 1, but in its contracted state.

FIG. 2 shows the embodiment of FIG. 1, but in its contracted state. The annular shape is maintained while the diameter is reduced by perhaps 20-30%. This reduction could vary on alternate embodiments depending on the number of base ring segments (2) and the change in distance separating them between the expanded and contracted states. A distance between the pair of legs is reduced when the corresponding flexing member flexes inwardly toward the central point as shown, and conversely increased when the corresponding flexing member flexes outwardly away from the central point. The base ring segments (2) and insets (4) are brought closer together circumferentially. The knees (6) flex upward to bring the legs (8) horizontal toward the height of the base ring. This movement of the legs could reduce the height by 10-50% based on the length of the legs (8). The legs (8) and ankles (12) are brought together in their pairs (10) by their feet (14). Each foot (14) is contracted by its ends coming together, and its body elongating downwards. As can be seen in FIG. 2, an interference between corresponding flexing members prevents the corresponding flexing member from being flexed fully inwardly to the plane.

Figure 3:
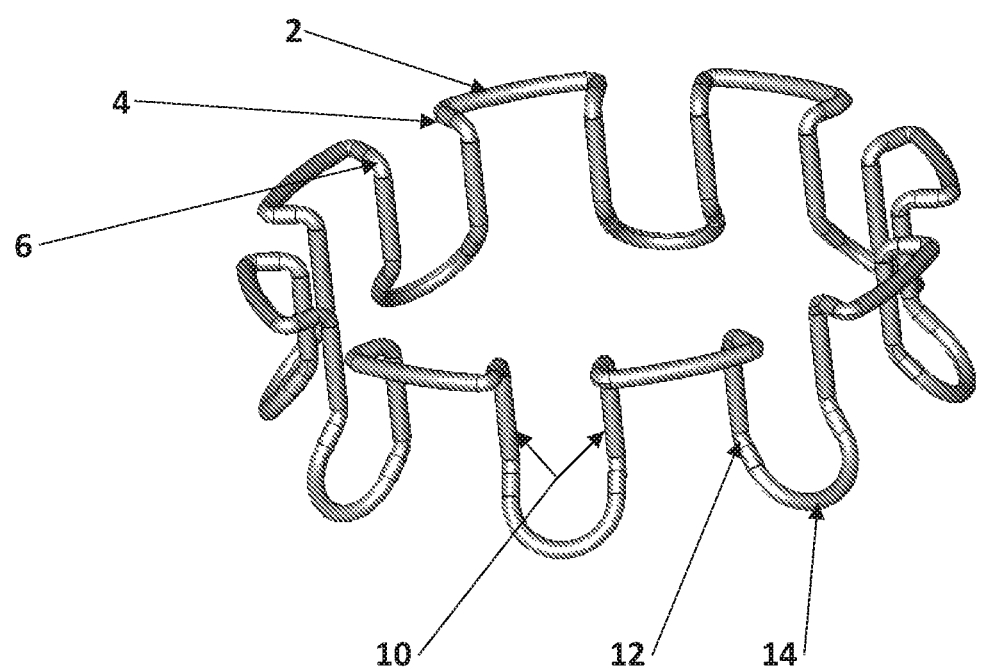
FIG. 3 shows a similar embodiment to FIG. 1 containing more leg pairs with accompanying components.

FIG. 3 shows a similar embodiment to FIG. 1 containing more leg pairs (10) with accompanying components: insets (4), knees (6), ankles (12), and feet (14). The base ring segments (2) are shortened to allow a similar diameter to that seen in FIG. 1. Specifically, the embodiment of FIG. 3 has eight segments (2) and eight leg pairs (10).

Figure 4:
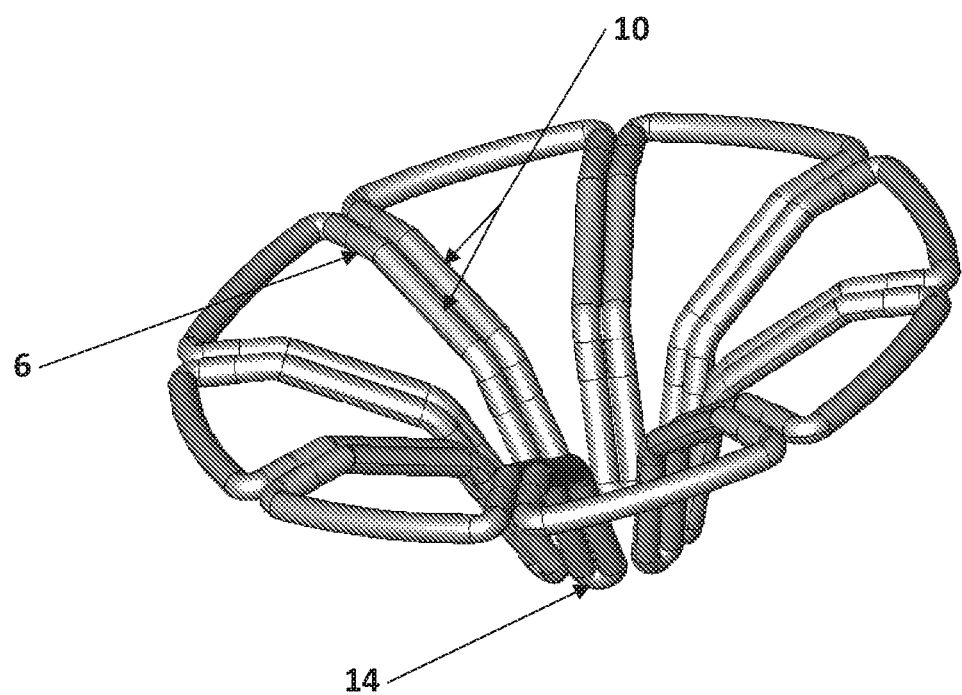
FIG. 4 shows the embodiment of FIG. 3 in its contracted state.

FIG. 4 shows the embodiment of FIG. 3 in its contracted state. Its similar diameter with FIG. 2 creates interference between the increased number of feet (14). This keeps the knees (6) from flexing the leg pairs (10) to a full horizontal position.

Figure 5:
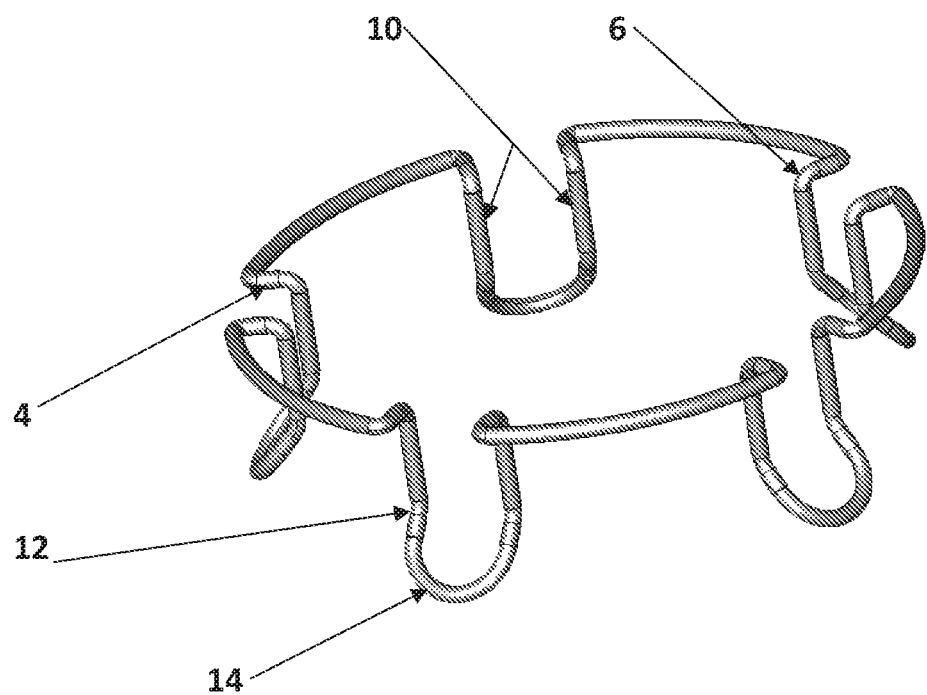
FIG. 5 shows a similar embodiment to FIG. 1 containing fewer leg pairs with accompanying components.

FIG. 5 shows a similar embodiment to FIG. 1 containing fewer leg pairs (10), five in this example, with accompanying components: insets (4), knees (6), ankles (12), and feet (14). The base ring segments (2) are longer to allow a similar diameter to that seen in FIG.

Figure 6:
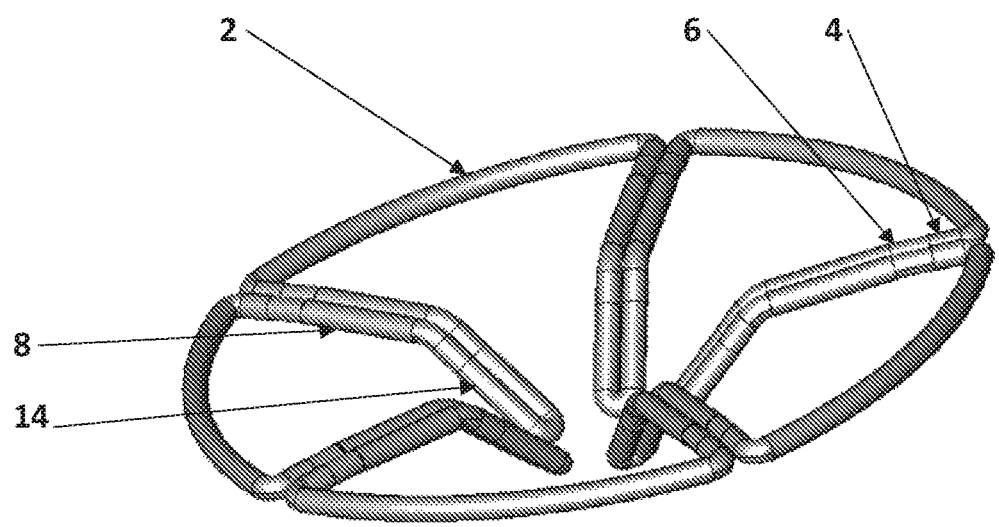
FIG. 6 shows the embodiment of FIG. 5 in its contracted state.

FIG. 6 shows the embodiment of FIG. 5 in its contracted state.

Figure 7:
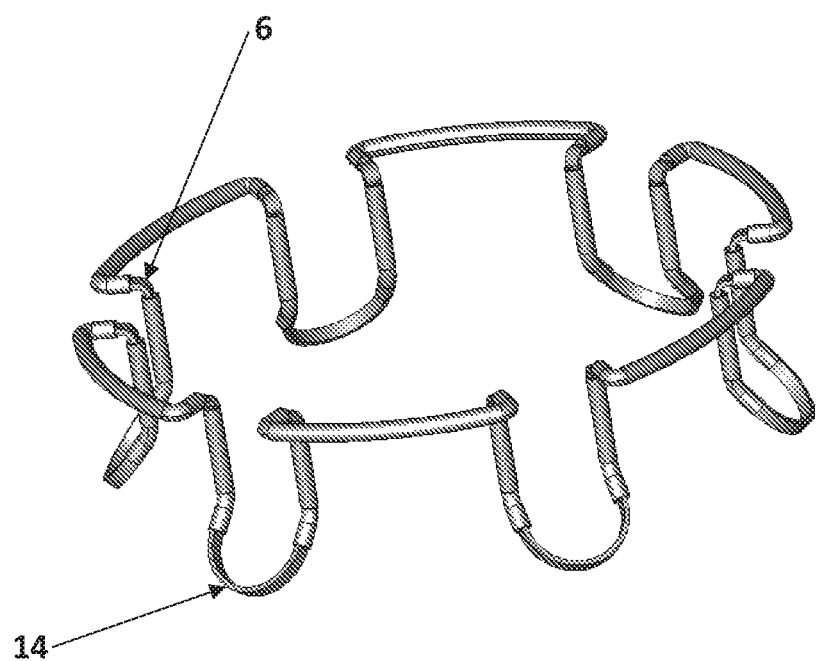
FIG. 7 shows another embodiment similar to FIG. 1 except that the knees and feet are changed for a flattened cross-section to potentially change the flexibility characteristics.

FIG. 7 shows another embodiment similar to FIG. 1 except that the knees (6) and feet (14) are changed for a flattened cross-section to potentially change the flexibility characteristics.

Figure 8:
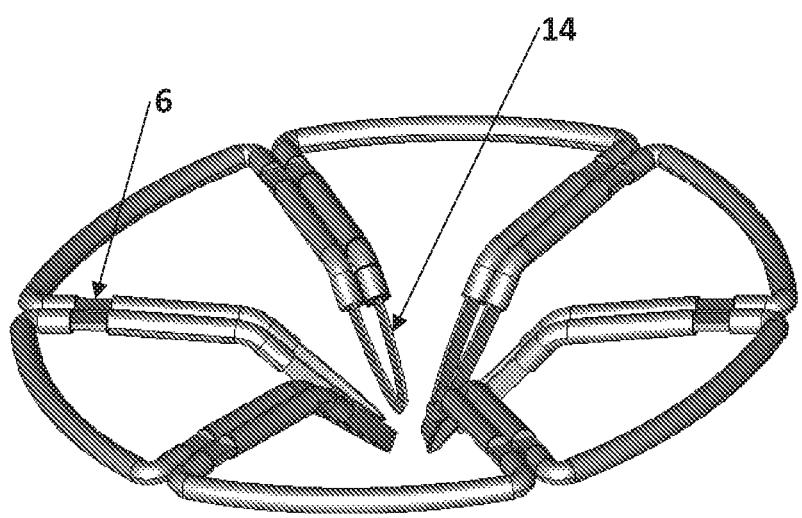
FIG. 8 shows the embodiment of FIG. 7 in its contracted state.

FIG. 8 shows the embodiment of FIG. 7 in its contracted state.

Figure 9:
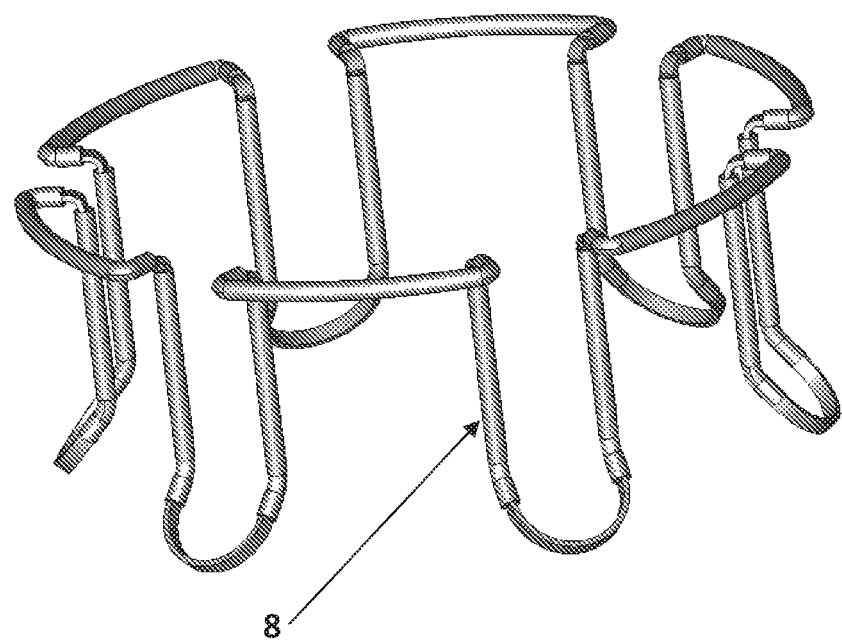
FIG. 9 shows another embodiment similar to FIG. 7 except the legs are of a medium length.

FIG. 9 shows another embodiment similar to FIG. 7 except the legs (8) are of a medium length. The medium length could add 50% to the leg length.

Figure 10:
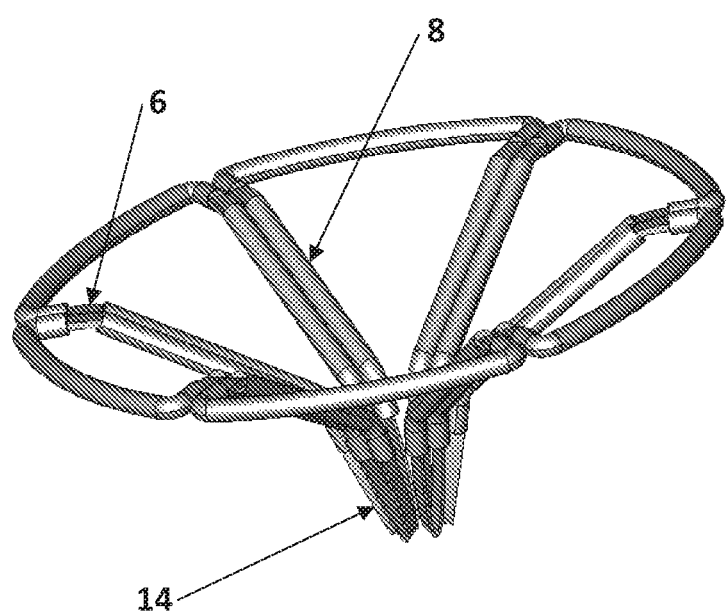
FIG. 10 shows the embodiment from FIG. 9 in its contracted state.

FIG. 10 shows the embodiment of FIG. 9 in its contracted state. The medium leg length on this embodiment, with its base ring diameter, causes interference between the feet (14) when contracted which does not allow the knees (6) to flex fully upwards to bring the legs (8) horizontal.

Figure 11:
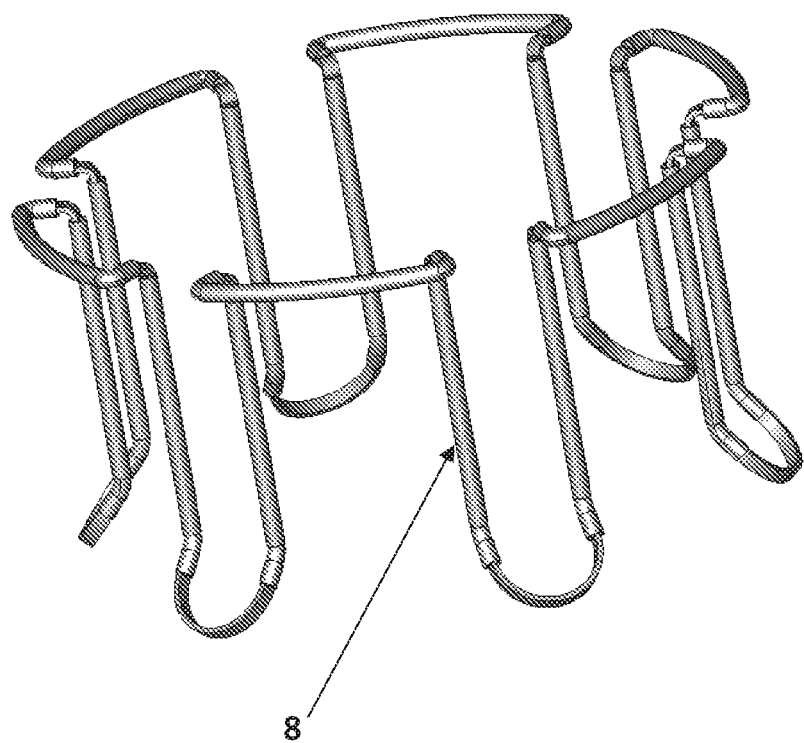
FIG. 11 shows another embodiment similar to FIG. 7 except the legs are of a long length.

FIG. 11 shows another embodiment similar to FIG. 7 except the legs (8) are of a long length. The long length could add 100% to the leg length.

Figure 12:
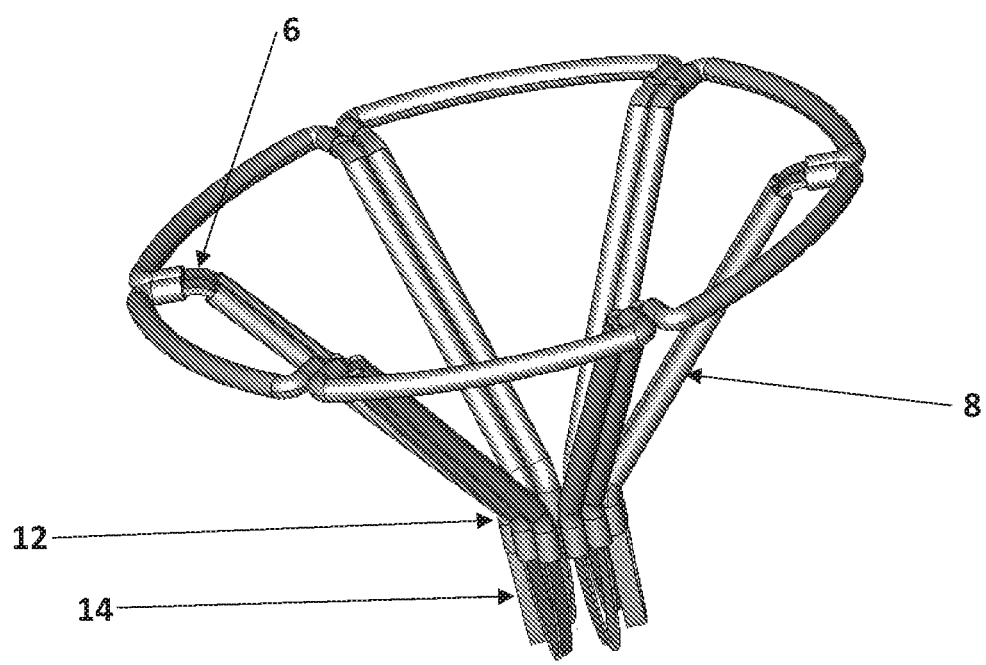
FIG. 12 shows the embodiment from FIG. 11 in its contracted state.

FIG. 12 shows the embodiment of FIG. 11 in its contracted state. The long leg length on this design, with its base ring diameter, causes interference between the ankles (12) and feet (14) when contracted which does not allow the knees (6) to flex fully upwards to bring the legs (8) horizontal.

Figure 13:
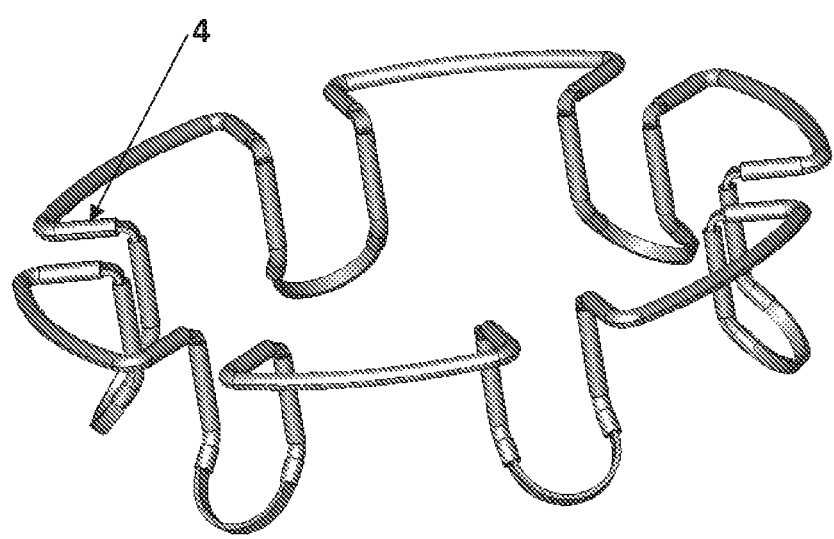
FIG. 13 shows another embodiment similar to FIG. 7 except that the inset is a medium length.

FIG. 13 shows another embodiment similar to FIG. 7 except that the inset (4) is a medium length. This medium length could be one eighth of the outer diameter of the base ring.

Figure 14:
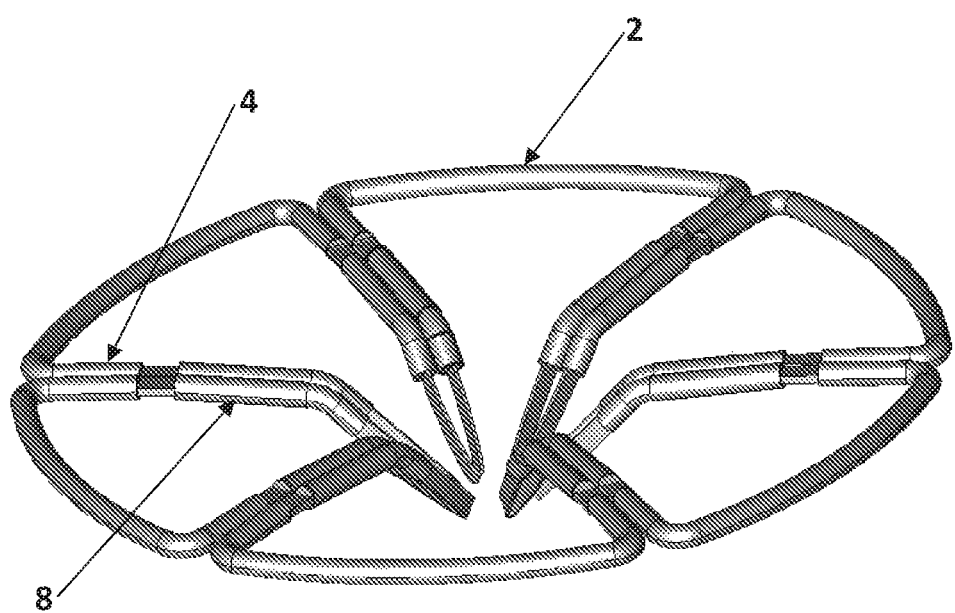
FIG. 14 shows the embodiment of FIG. 13 in its contracted state.

FIG. 14 shows the embodiment of FIG. 13 in its contracted state. The increased inset (4) length is added to the outer diameter of the base ring and not moving the legs (8) inward where it would cause quicker interference between the various parts. The base ring segments (2) are elongated to satisfy this larger diameter.

Figure 15:
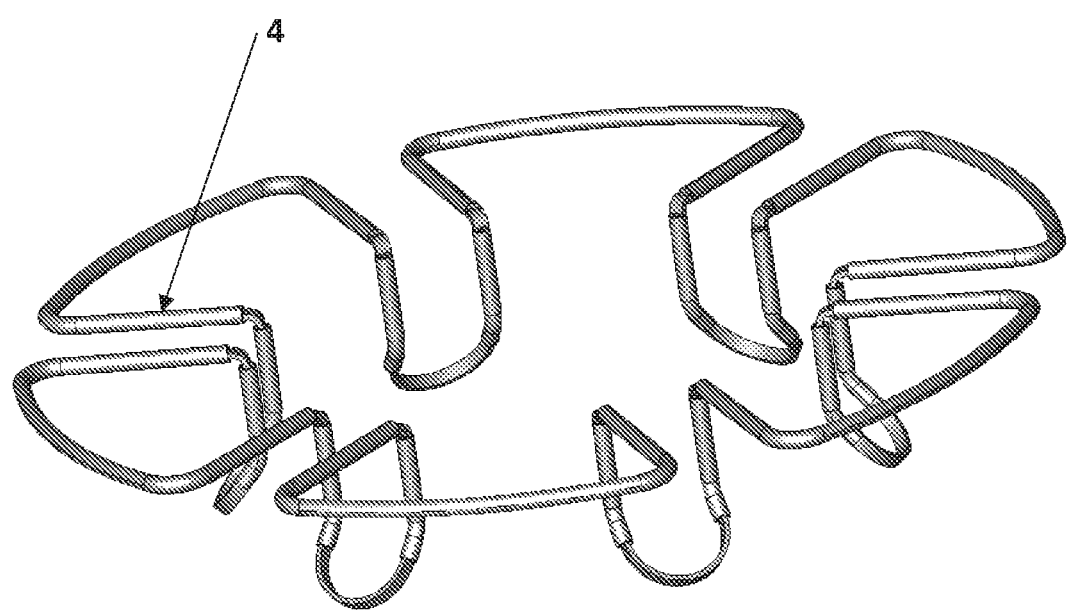
FIG. 15 shows another embodiment similar to FIG. 7 except that the inset is a long length.

FIG. 15 shows another embodiment similar to FIG. 7 except that the inset (4) is a long length. This long length could be one fourth of the outer diameter of the base ring.

Figure 16:
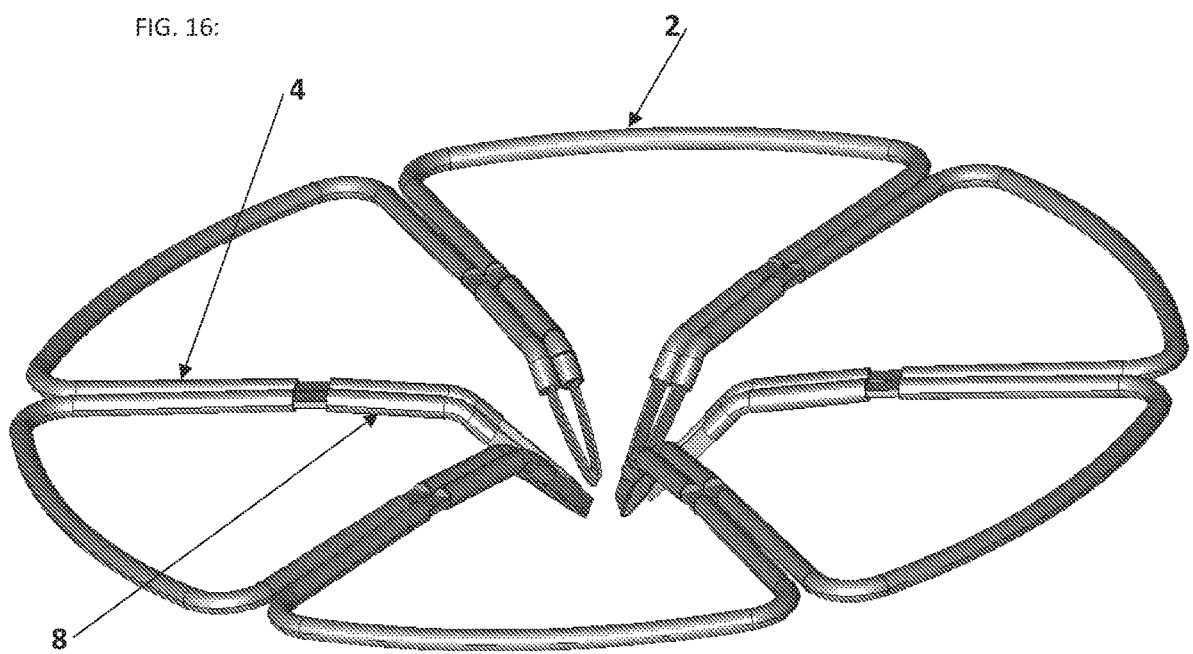
FIG. 16 shows the embodiment of FIG. 15 in its contracted state.

FIG. 16 shows the embodiment of FIG. 15 in its contracted state. The increased inset (4) length is added to the outer diameter of the base ring and not moving the legs (8) inward where it would cause quicker interference between the various parts. The base ring segments (2) are elongated to satisfy this larger diameter.

Figure 17:
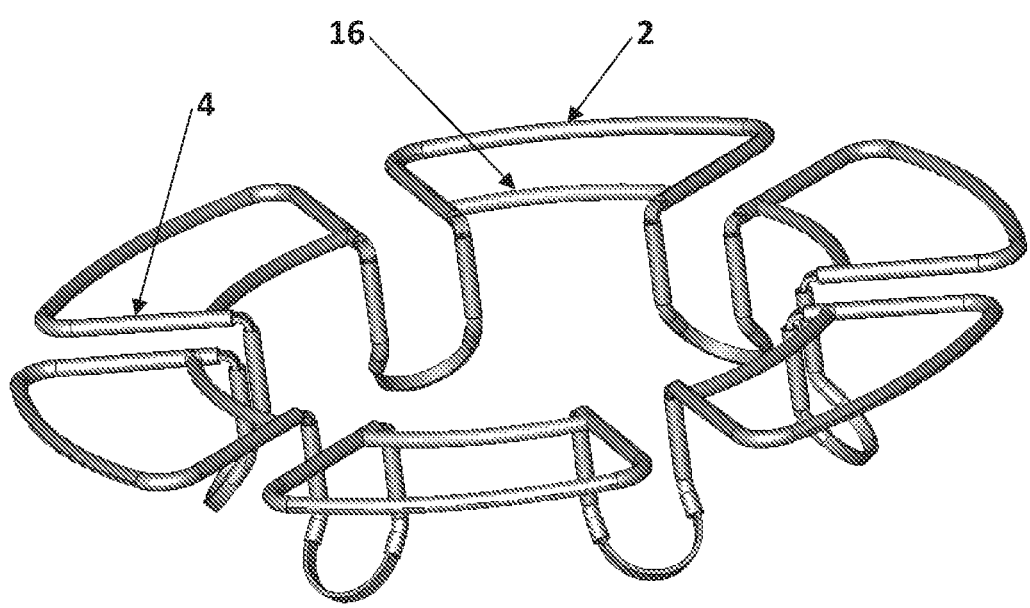
FIG. 17 shows another embodiment similar to FIG. 15 with a support strut added between the central ends of the insets attached to the same base ring segment.

FIG. 17 shows another embodiment similar to FIG. 15 with a support strut (16) added between the central ends of the insets (4) attached to the same base ring segment (2). This support strut adds stability to the base ring form when necessary.

Figure 18:
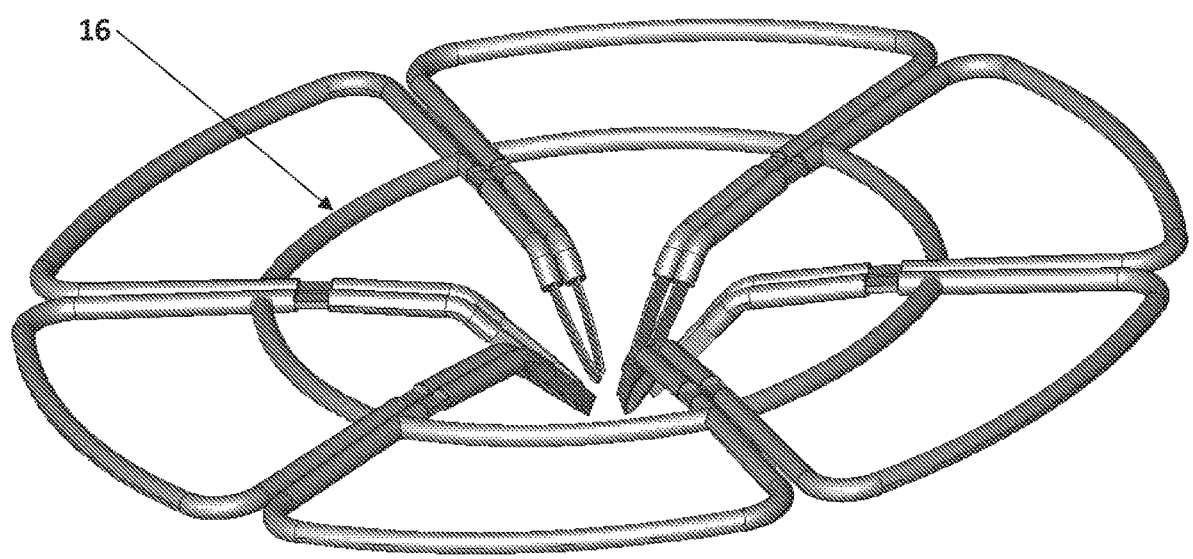
FIG. 18 shows the embodiment from FIG. 17 in its contracted state.

FIG. 18 shows the embodiment of FIG. 17 in its contracted state. The support strut (16) does not change any other dimensions of this design.

Figure 19:
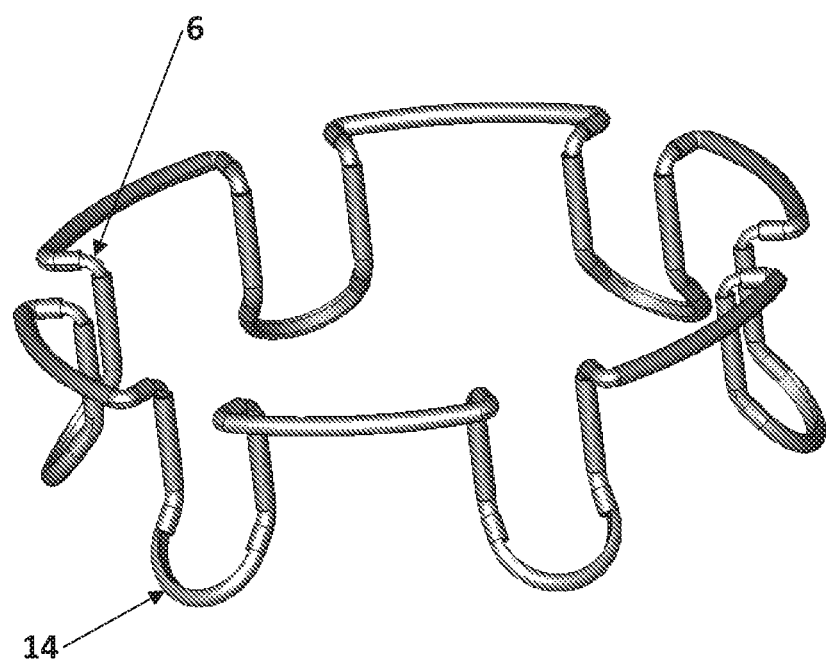
FIG. 19 shows another embodiment similar to FIG. 7 except that the knees and feet are changed for a semi-round cross-section to potentially change the flexibility characteristics.

FIG. 19 shows another embodiment similar to FIG. 7 except that the knees (6) and feet (14) are changed for a semi-round cross-section to potentially change the flexibility characteristics.

Figure 20:
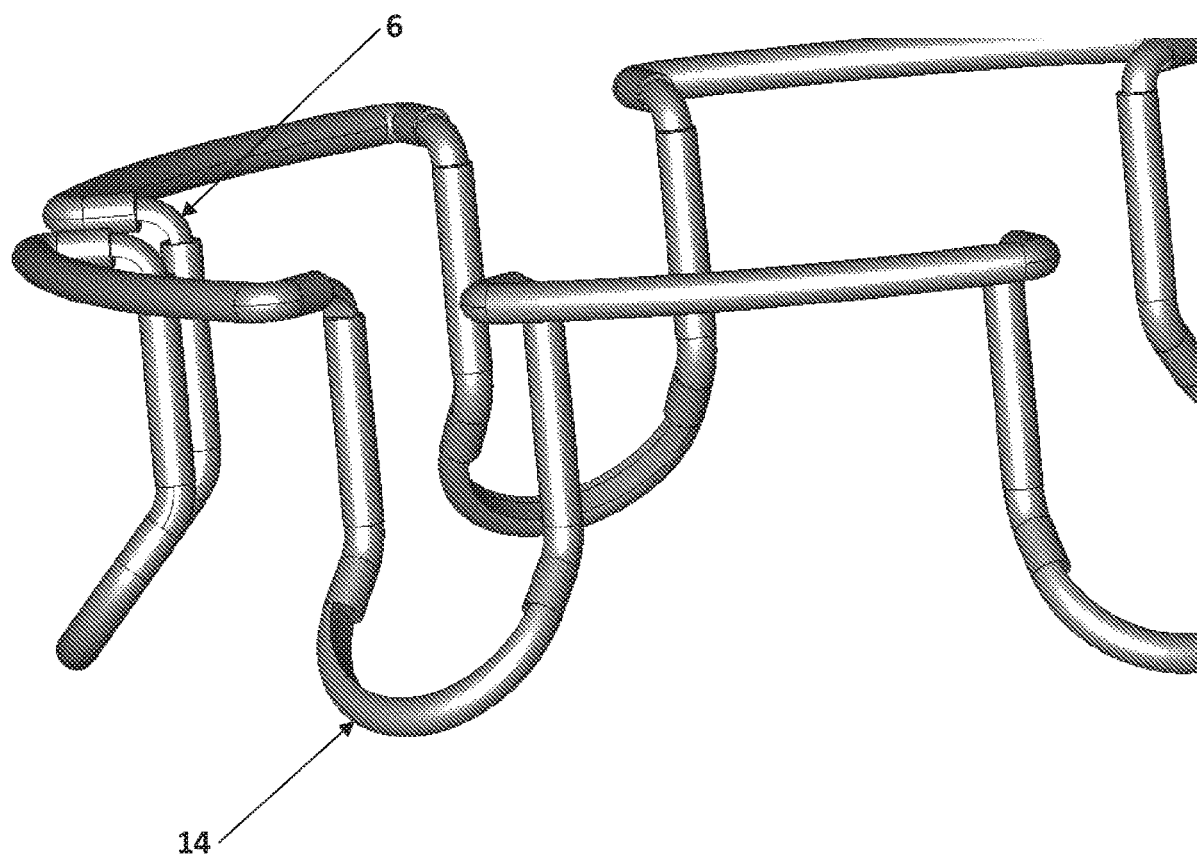
FIG. 20 shows a closer view of the semi-round knees and feet from FIG. 19.

FIG. 20 shows a closer view of the semi-round knees (6) and feet (14) from FIG. 19.

Figure 21:
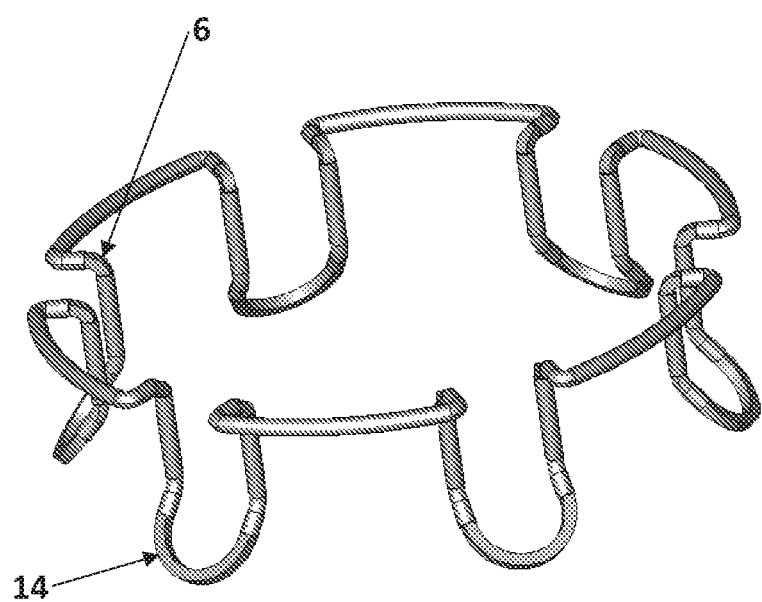
FIG. 21 shows another embodiment similar to FIG. 7 except that the knees and feet are changed for a square cross-section to potentially change the flexibility characteristics.

FIG. 21 shows another embodiment similar to FIG. 7 except that the knees (6) and feet (14) are changed for a square cross-section to potentially change the flexibility characteristics.

Figure 22:
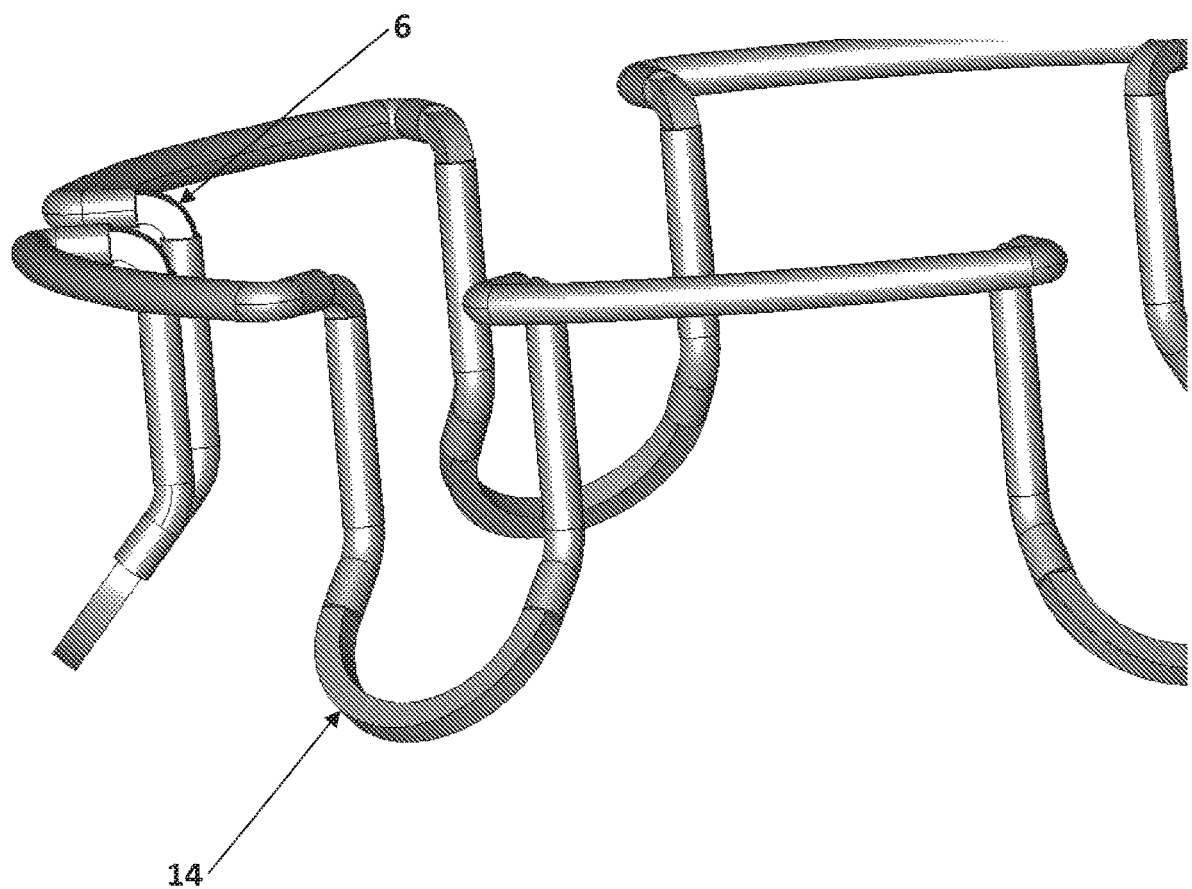
FIG. 22 shows a closer view of the square knees and feet from FIG. 21.

FIG. 22 shows a closer view of the square knees (6) and feet (14) from FIG. 21.

Figure 23:
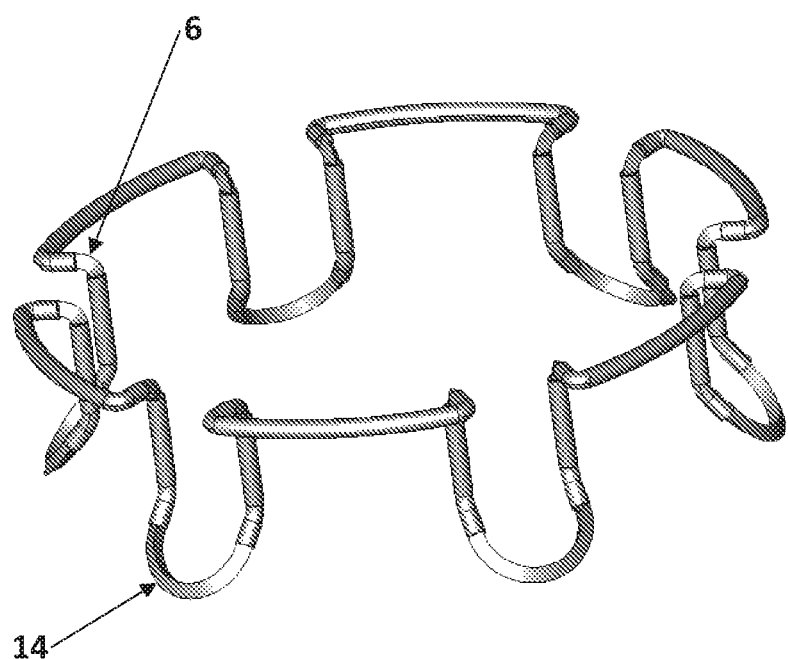
FIG. 23 shows another embodiment similar to FIG. 7 except that the knees and feet are changed for a triangular cross-section to potentially change the flexibility characteristics.

FIG. 23 shows another embodiment similar to FIG. 7 except that the knees (6) and feet (14) are changed for a triangular cross-section to potentially change the flexibility characteristics.

Figure 24:
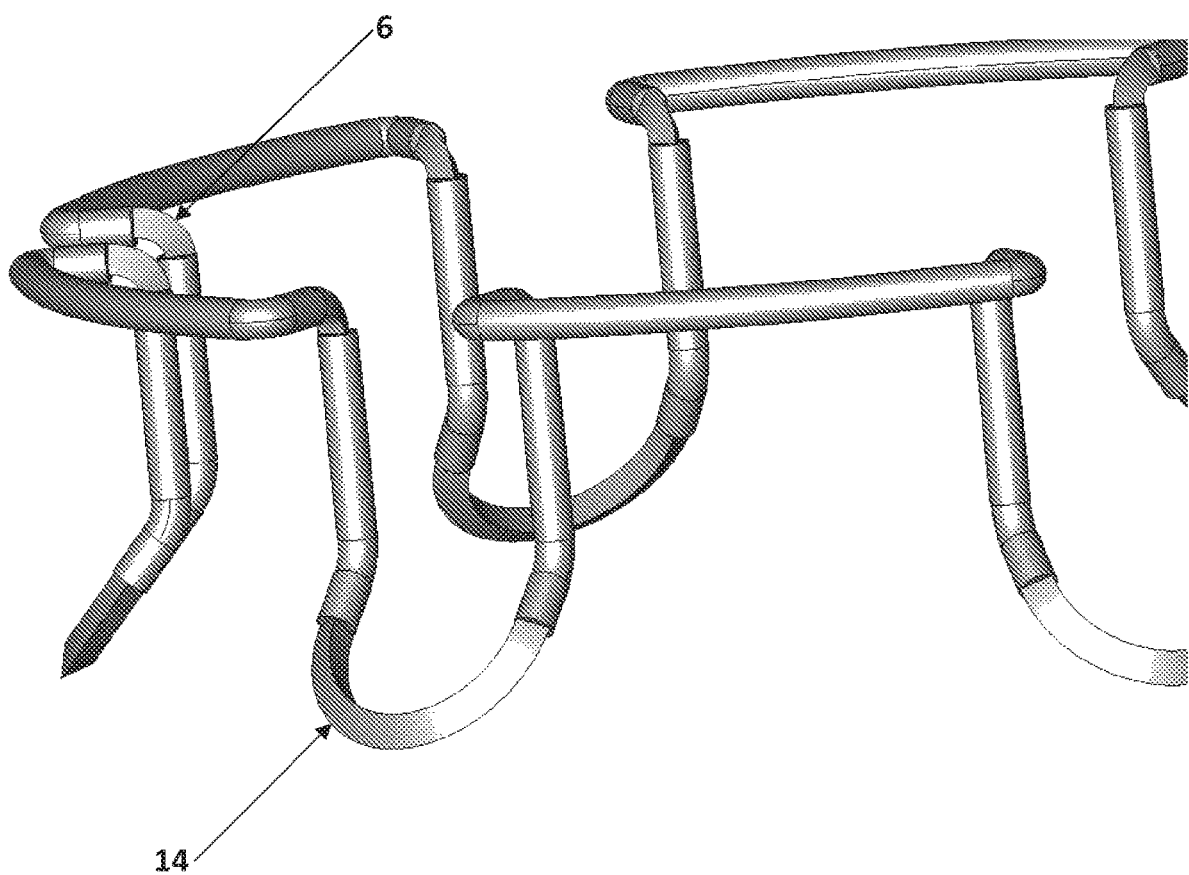
FIG. 24 shows a closer view of the triangular knees and feet from FIG. 23.

FIG. 24 shows a closer view of the triangular knees (6) and feet (14) from FIG. 23.

Figure 25:
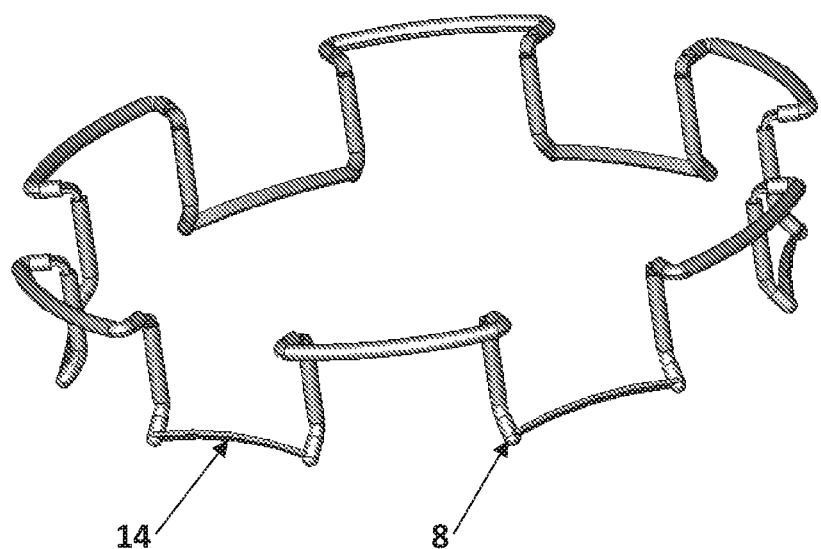
FIG. 25 shows another embodiment similar to FIG. 7 except the feet are reversed to bend upward when contracted.

FIG. 25 shows another embodiment similar to FIG. 7 except the feet (14) are reversed to bend upward when contracted. The bottom end of the legs (8) are finished with a rounded end.

Figure 26:
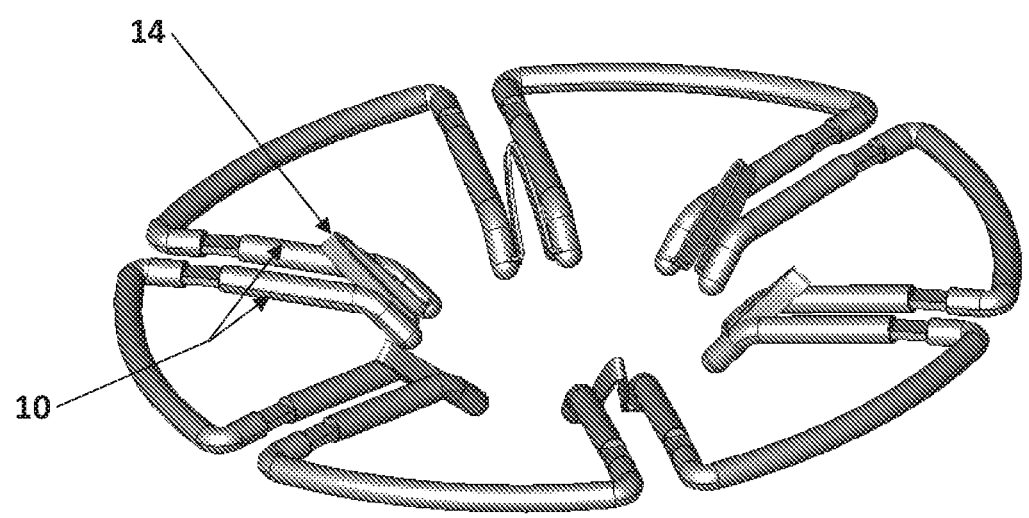
FIG. 26 shows the embodiment from FIG. 25 in its contracted state.

FIG. 26 shows the embodiment of FIG. 25 in its contracted state. Of note are the upward contracted feet (14) and the space between the contracted legs pairs (10) that accommodates each foot.

Figure 27:
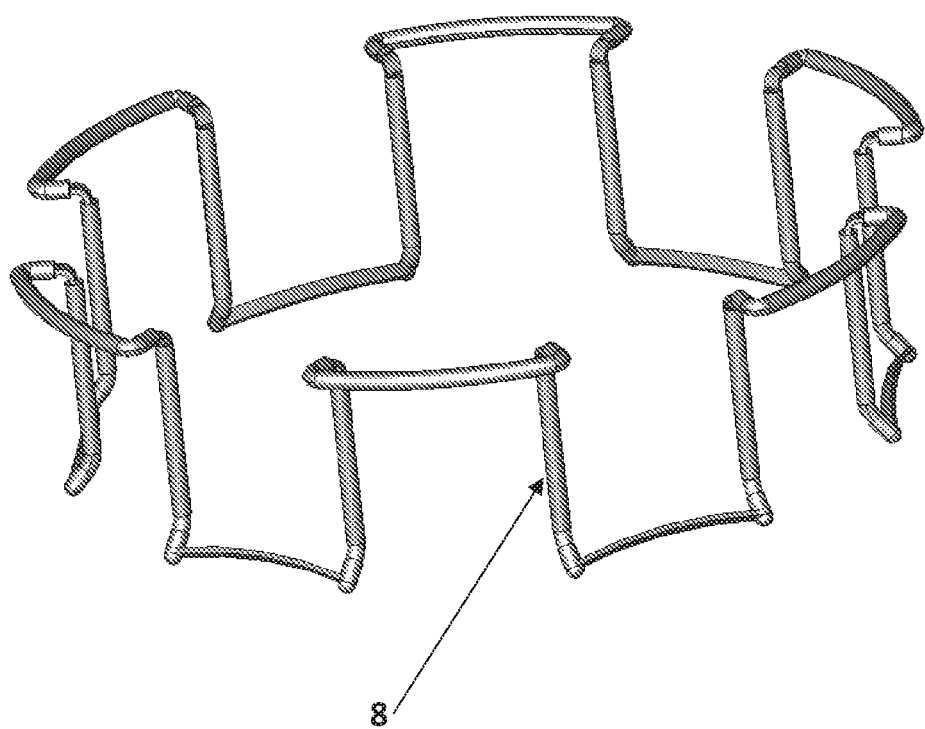
FIG. 27 shows another embodiment similar to FIG. 25 except the legs are of a medium length.

FIG. 27 shows another embodiment similar to FIG. 25 except the legs (8) are of a medium length. The medium length could add 50% to the leg length.

Figure 28:
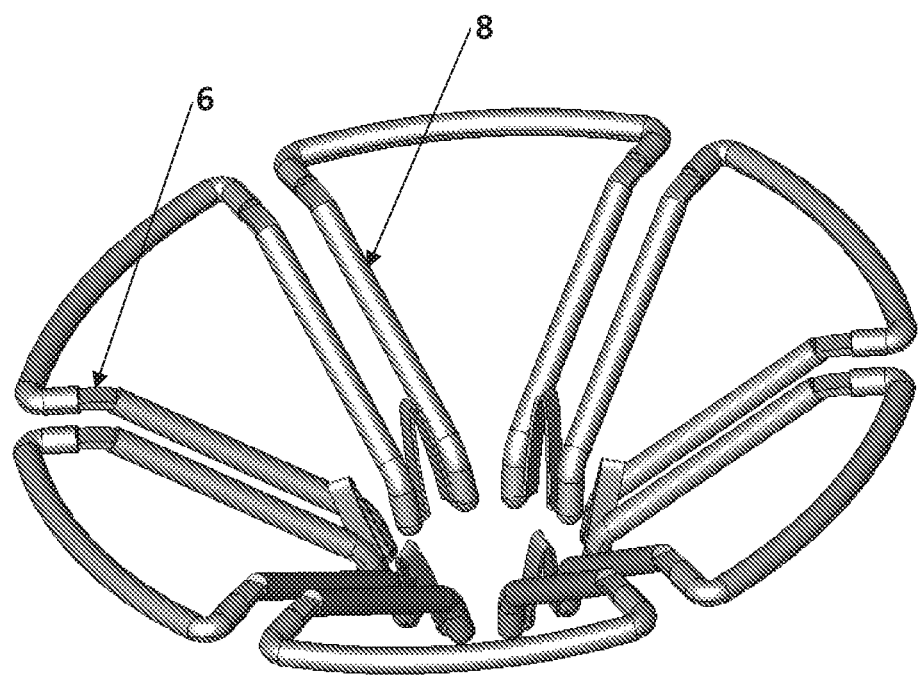
FIG. 28 shows the embodiment from FIG. 27 in its contracted state.

FIG. 28 shows the embodiment of FIG. 27 in its contracted state. The medium leg length on this design, with its base ring diameter, causes interference between the legs (8) when contracted which does not allow the knees (6) to flex fully upwards to bring the legs (8) horizontal.

Figure 29:
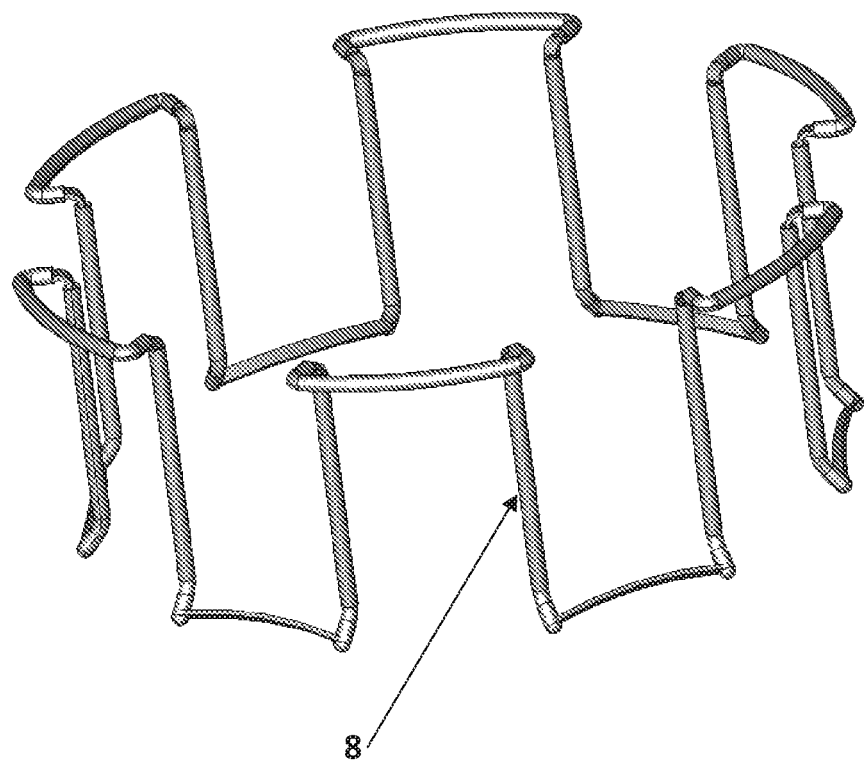
FIG. 29 shows another embodiment similar to FIG. 25 except the legs are of a long length.

FIG. 29 shows another embodiment similar to FIG. 25 except the legs (8) are of a long length. The long length could add 100% to the leg length.

Figure 30:
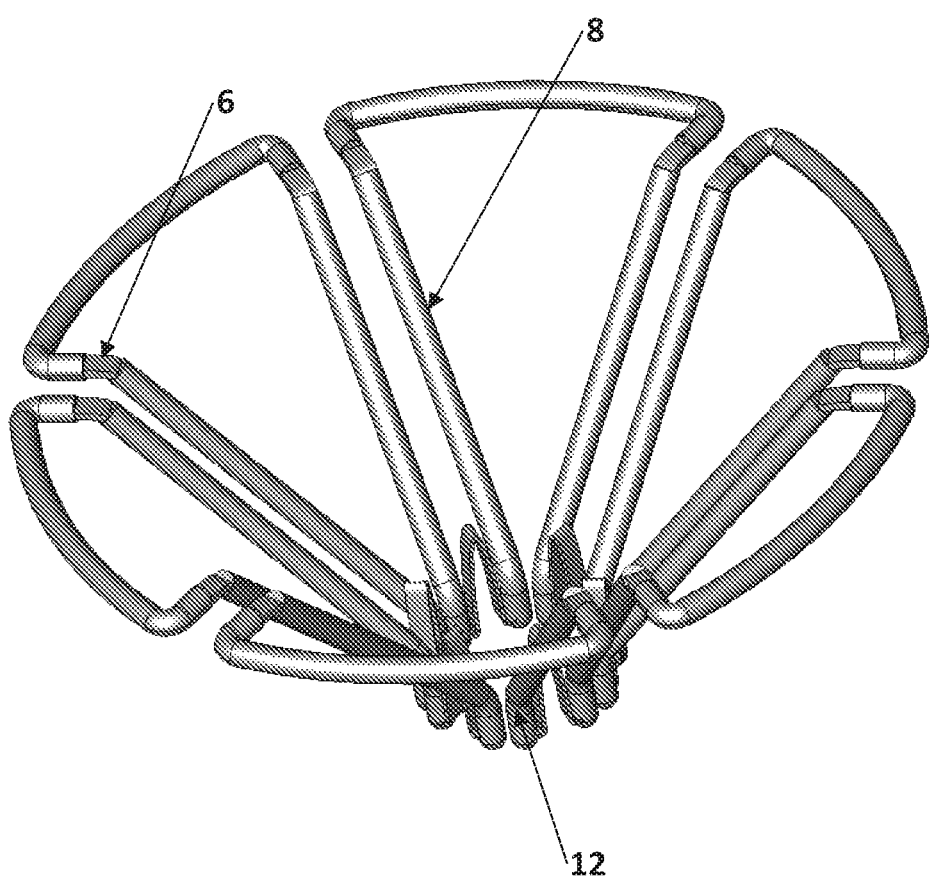
FIG. 30 shows the embodiment from FIG. 29 in its contracted state.

FIG. 30 shows the embodiment of FIG. 29 in its contracted state. The long leg length on this design, with its base ring diameter, causes interference between the legs (8) and ankles (12) when contracted which does not allow the knees (6) to flex fully upwards to bring the legs (8) horizontal.

Figure 31:
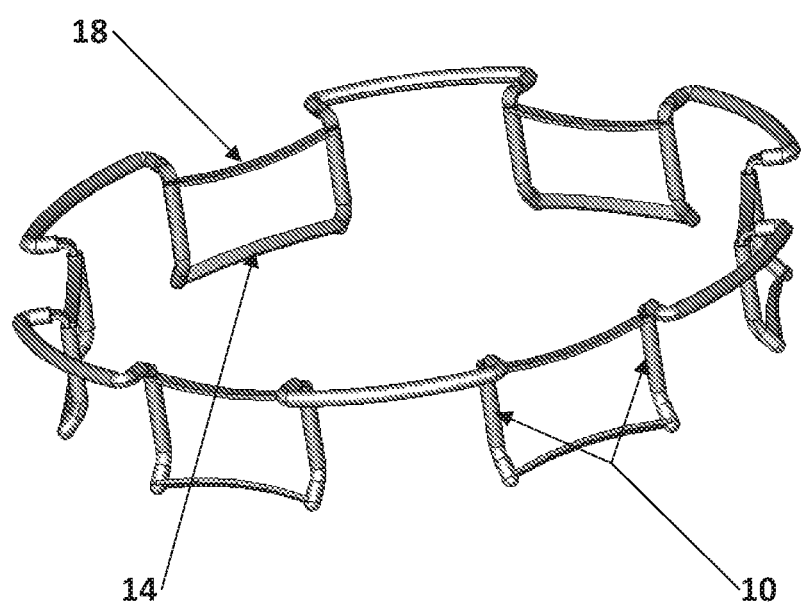
FIG. 31 shows a possible design similar to FIG. 25 with an additional expansion strut with a similar design to the foot added between the leg pairs.

FIG. 31 shows another embodiment similar to FIG. 25 with an additional expansion strut (18) with a similar design to the foot (14) added between the leg pairs (10). This could add additional force for expanding the ring diameter when used.

Figure 32:
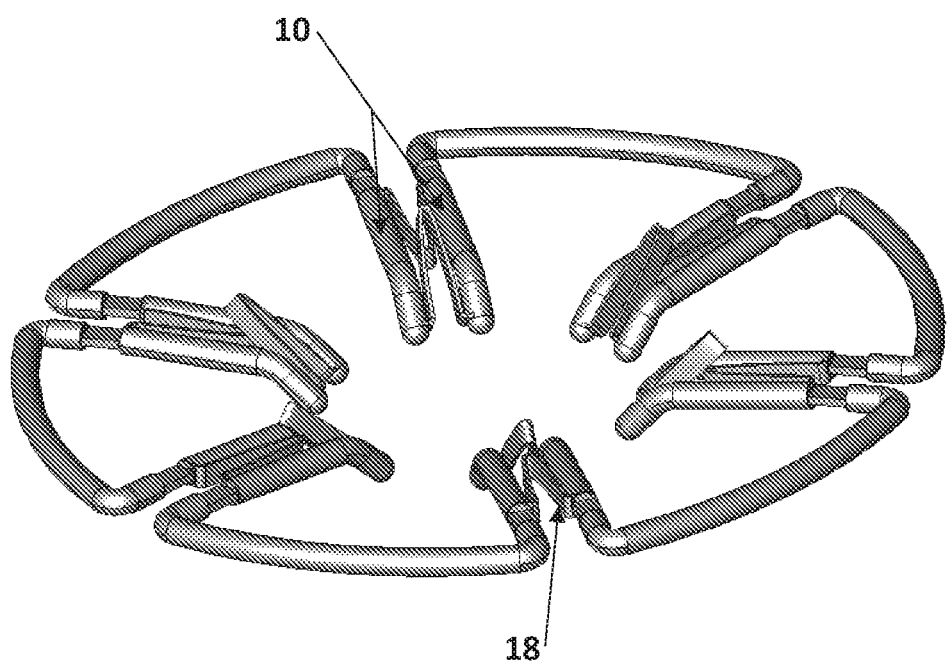
FIG. 32 shows the embodiment from FIG. 31 in its contracted state.

FIG. 32 shows the embodiment of FIG. 31 in its contracted state. Of note are the expansion struts (18) contracted between the leg pairs (10) without interfering with other parts of the design.

Figure 33:
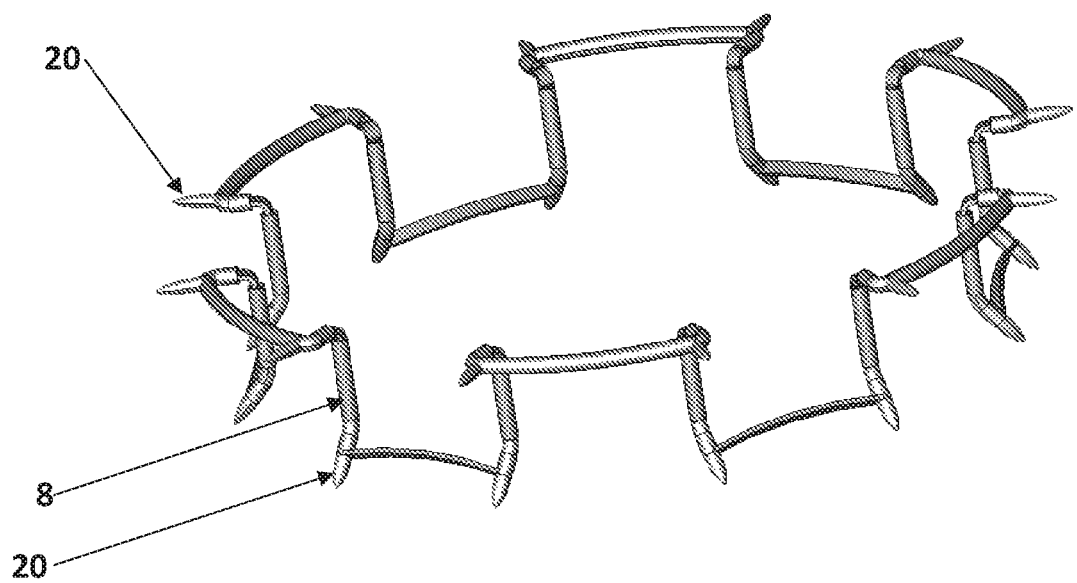
FIG. 33 shows another embodiment with additional traction devices.

FIG. 33 shows another embodiment with additional traction devices. These protrusions (20) are spaced around the base ring to add traction outside of the atria. Similar protrusions (20) may be added to the bottom ends of the legs (8) to add traction to the interior of the atrial wall.

Figure 34:
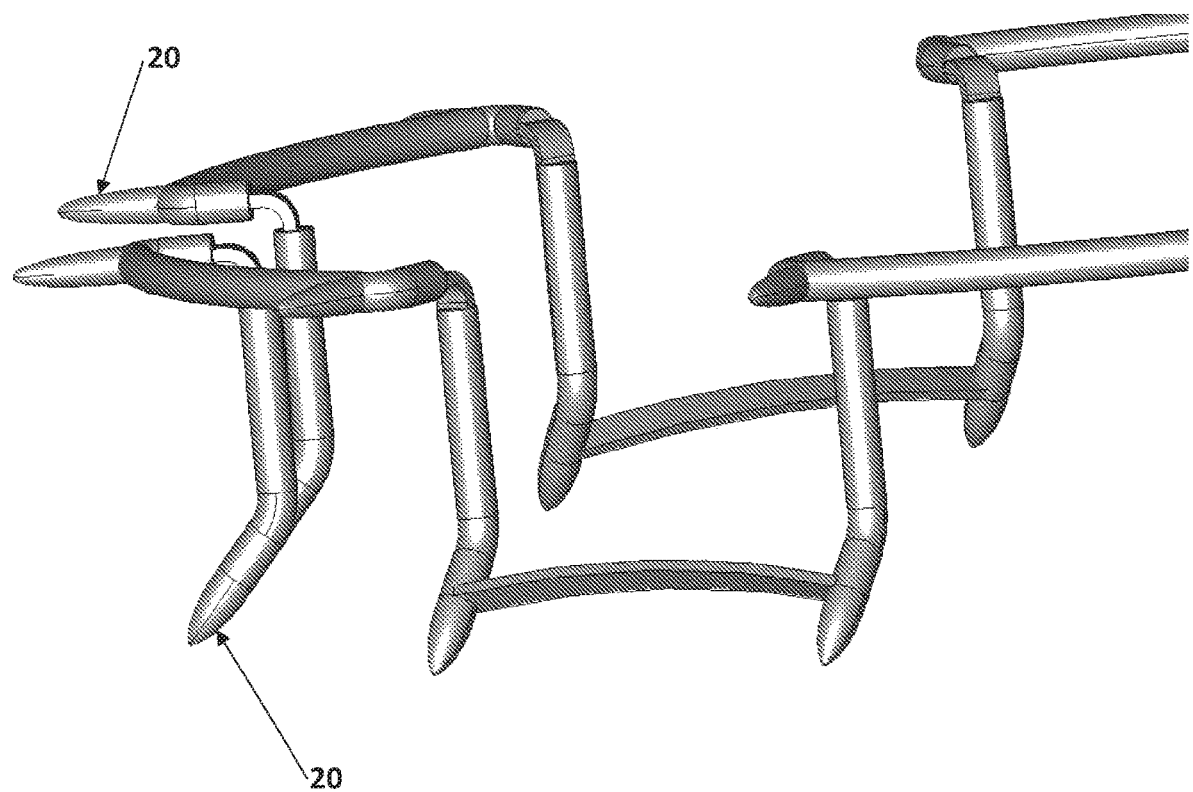
FIG. 34 shows a closer view of the protrusions from FIG. 33.

FIG. 34 shows a closer view of the protrusions (20) from FIG. 33.

Figure 35:
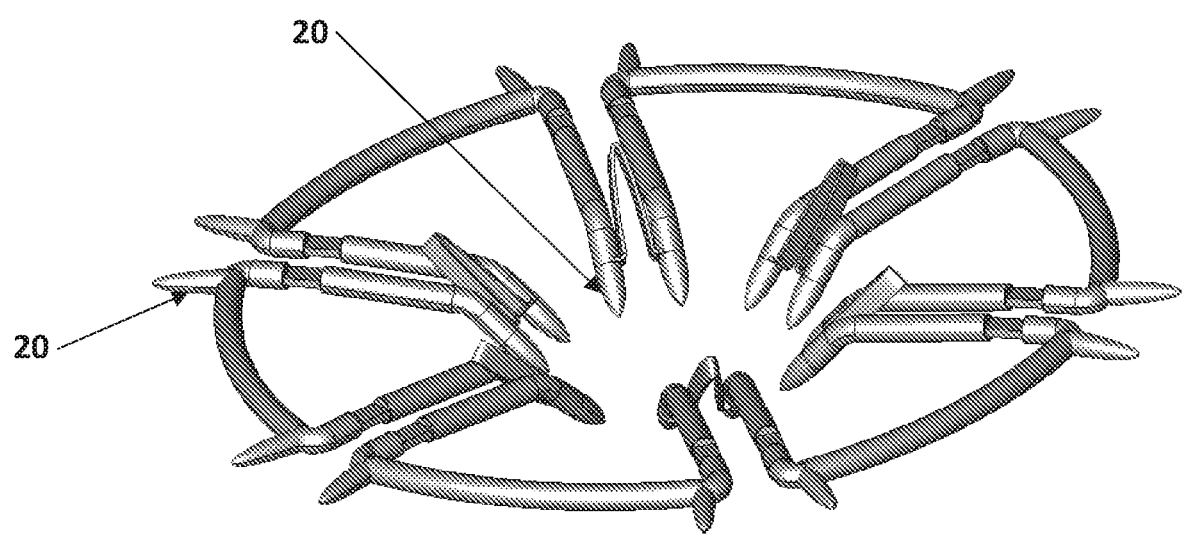
FIG. 35 shows the embodiment from FIG. 33 in its contracted state.

FIG. 35 shows the embodiment of FIG. 33 in its contracted state.

Figure 36:
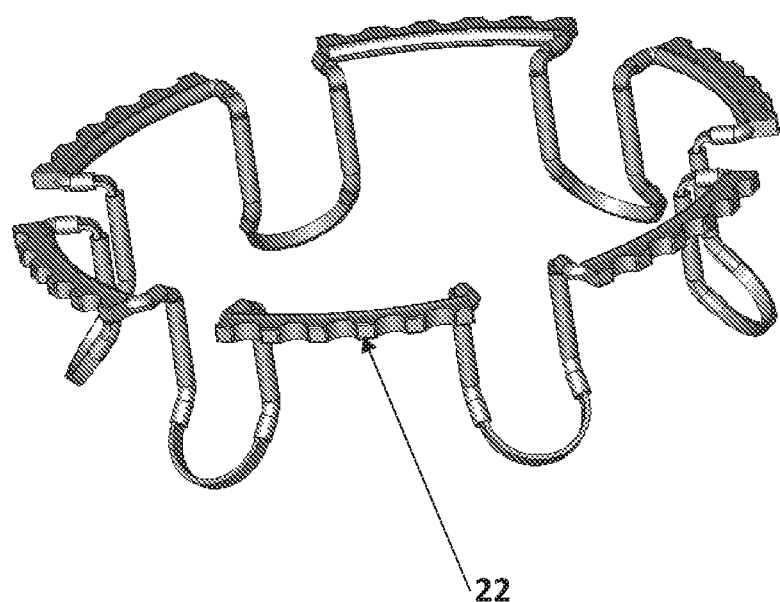
FIG. 36 shows another embodiment similar to FIG. 7 with base ring segments having traction segments along their outer dimensions.

FIG. 36 shows another embodiment similar to FIG. 7 with base ring segments having traction segments (22) along their outer dimensions.

Figure 37:
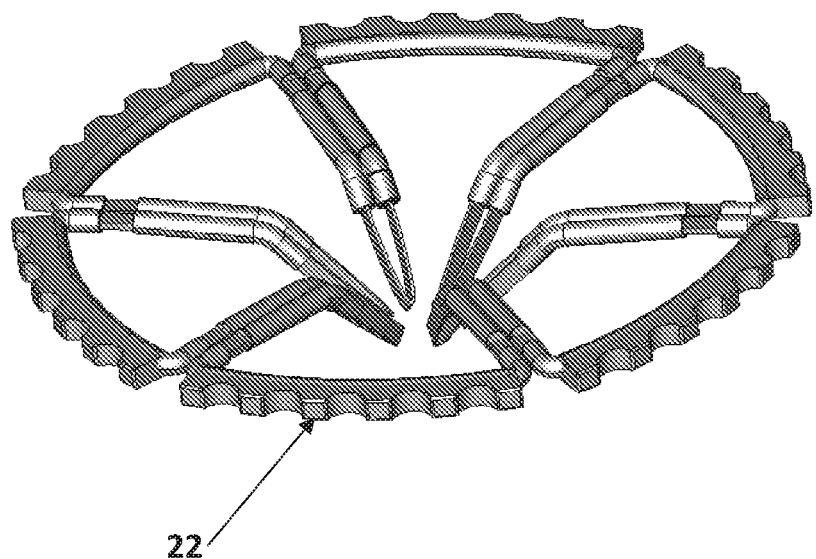
FIG. 37 shows the embodiment from FIG. 36 in its contracted state.

FIG. 37 shows the embodiment of FIG. 36 in its contracted state.

Figure 38:
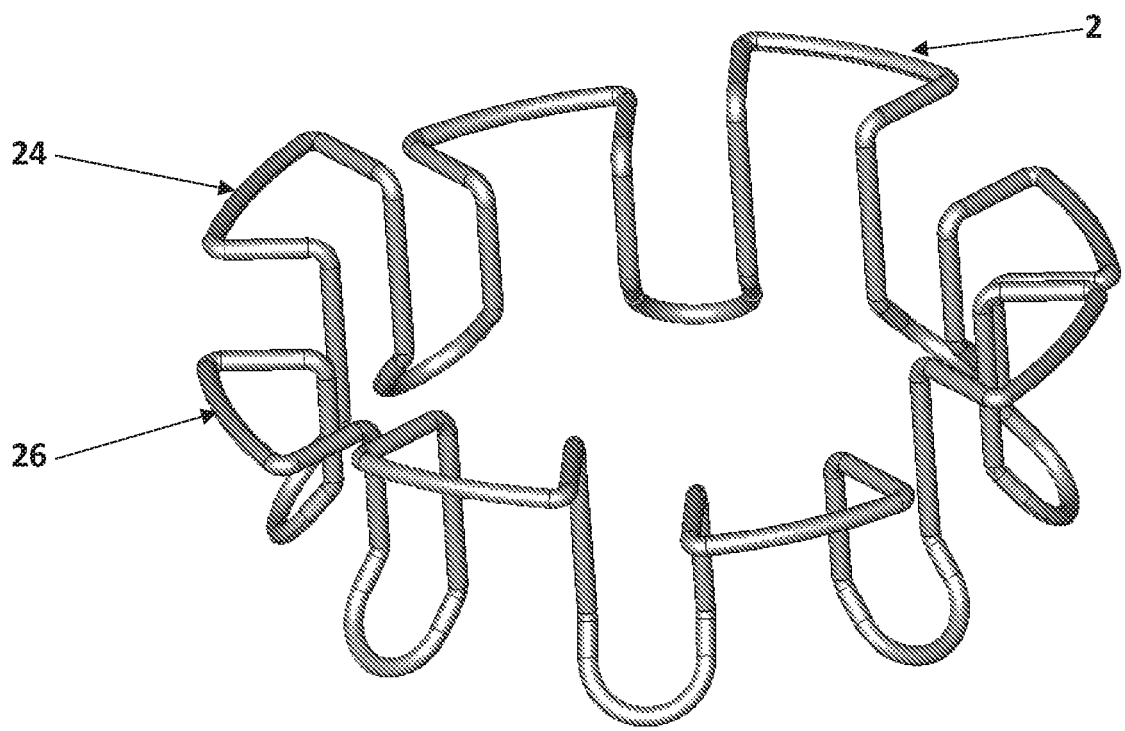
FIG. 38 shows a similar embodiment to FIG. 3 except that the alternating base ring segments are set at differing heights.

FIG. 38 shows another embodiment where the alternating base ring segments (2) are set at differing heights that could be 1-4 mm apart. This may allow for tissue to be held between the upper base ring segments (24) and lower base ring segments (26).

Figure 39:
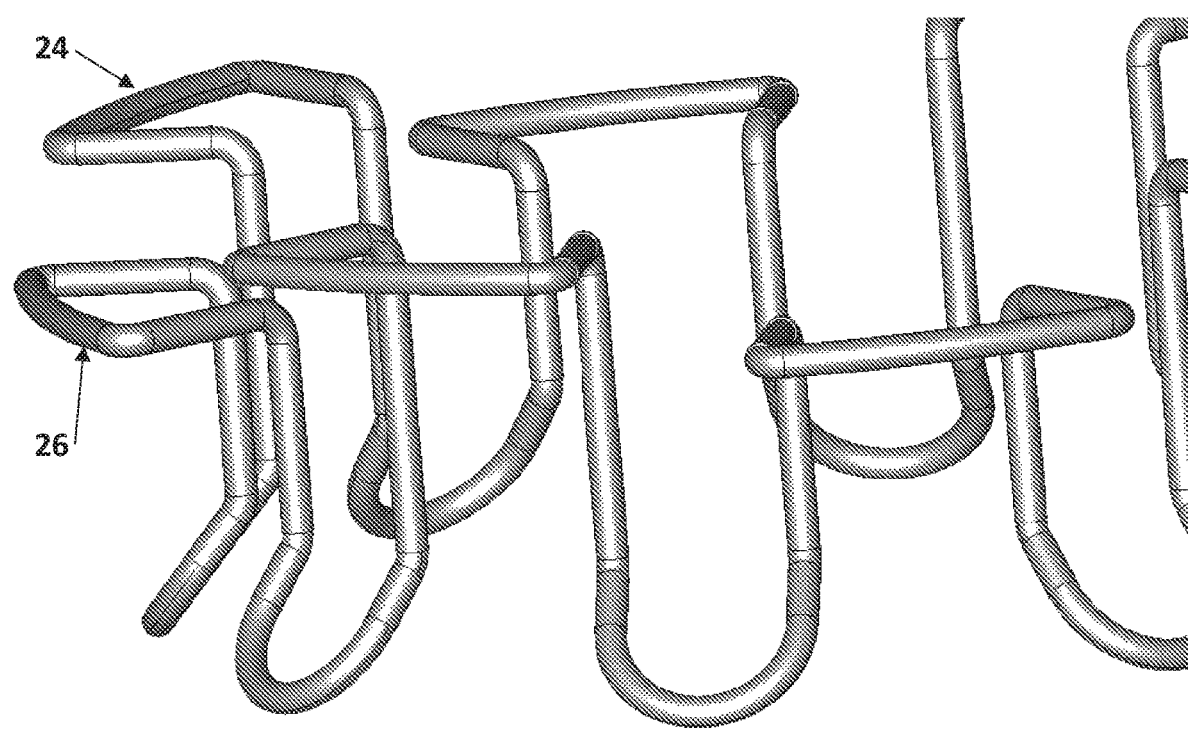
FIG. 39 shows a closer view of the base ring segments at differing heights from FIG. 38.

FIG. 39 shows a closer view of the upper base ring segments (24) and the lower base ring segments (26) from FIG. 38.

Figure 40:
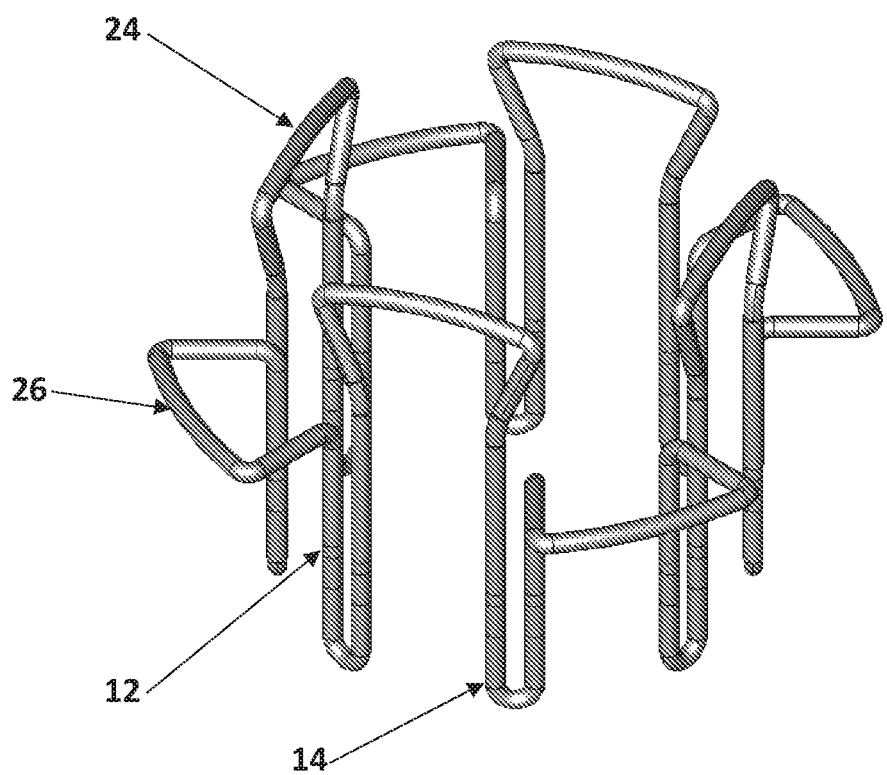
FIG. 40 shows the embodiment from FIG. 38 in a contracted state.

FIG. 40 shows the embodiment from FIG. 38 in a contracted state. The upper base ring segments (24) rotate upwards to a vertical position while the lower base ring segments (26) remain horizontal. The ankles (12) straighten to move the feet (14) into a vertical position.

Figure 41:
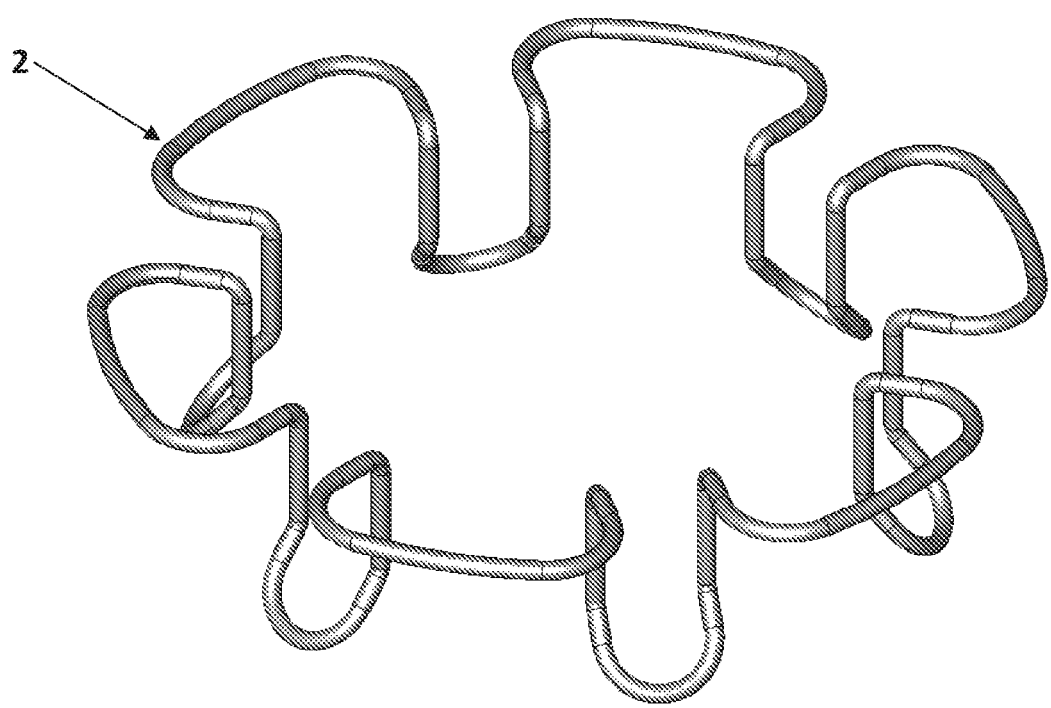
FIG. 41 shows a similar embodiment to FIG. 1 except that the bends at the ends of the base ring segments have been increased in radius.

FIG. 41 shows another embodiment similar to FIG. 1 except that the inward bends at the ends of the base ring segments (2) have been increased in radius by a factor of 30 to allow for a softer curve. Various increases from a factor of three to five to thirty may be used. This may allow for the bend to recover more easily from the contracted state.

Figure 42:
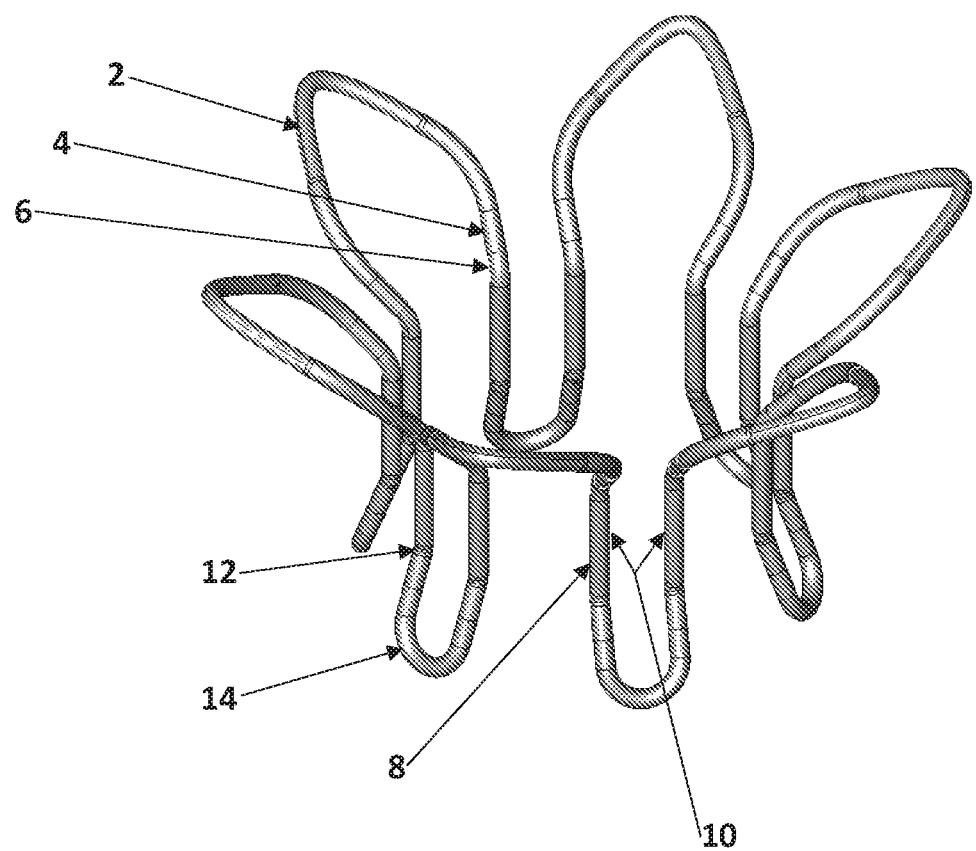
FIG. 42 shows the embodiment from FIG. 40 in a half-contracted state to show a possible alternative contracting method.

FIG. 42 shows the embodiment from FIG. 41 in a half-contracted state. As shown, the base ring segments (2) are bending inward from their midpoints and opening the bends at their ends. The knees (6) are rotating the base ring segments (2) and insets (4) upwards. The ankles (12) are straightening downward. The feet (14) are contracting pulling the legs (8) together in their pairs (10).

Figure 43:
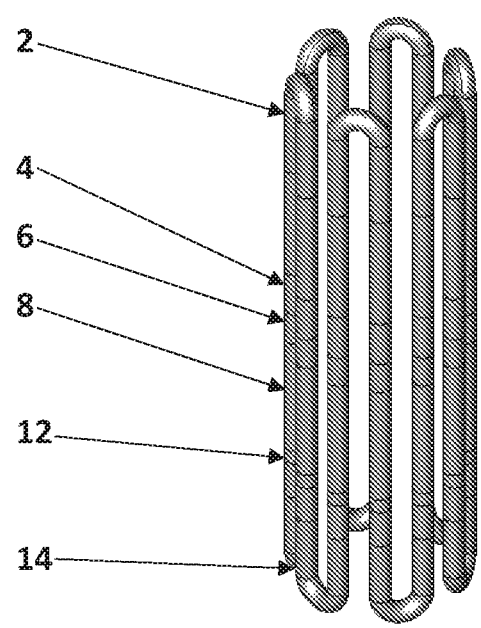
FIG. 43 shows the embodiment from FIG. 40 in a fully contracted state.

FIG. 43 show the embodiment from FIG. 41 in a contracted state. The base ring segments (2) have folded closed and rotated to a vertical position along with the insets (4). The knees (6) have straightened to a vertical position. The ankles (12) have straightened to a vertical position. The feet (14) have contracted, and together with the base ring segments, are pulling the legs (8) and other components together.

Figure 44:
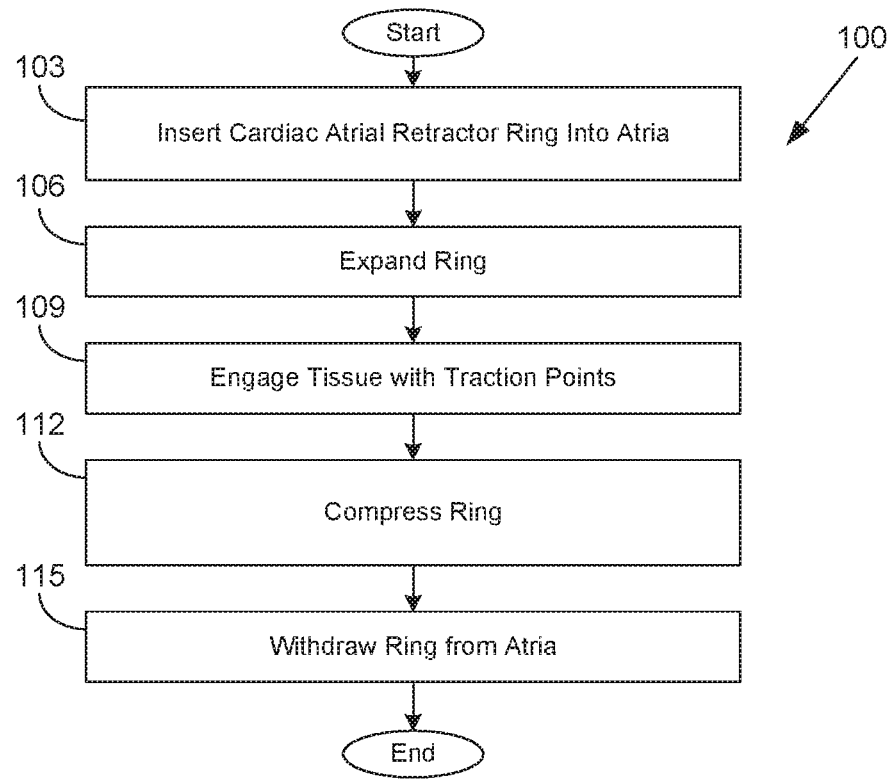
FIG. 44 is a flowchart illustrating an example method of use for one or more embodiments.

FIG. 44 is an example flowchart 100 illustrating a method of use for the cardiac atrial retractor ring. At 103, the cardiac atrial retractor ring is inserted into the atria when the cardiac atrial retractor ring is in a compressed position. For example, the cardiac atrial retractor ring may be inserted through a laparoscopic port. At 106, the cardiac atrial retractor ring is expanded into the expanded position, thereby retracting the atria. For example, the cardiac atrial retractor ring may be expanded into the expanded position in response to a change in temperature. At 109, striated fibril tissue of the atrium is engaged with a plurality of traction points surrounding the cardiac atrial retractor ring. At 112, the cardiac atrial retractor ring is compressed from the expanded position to the compressed position, for example, in response to a change in temperature. At 115, the cardiac atrial retractor ring is withdrawn from the atria.

Embodiments of the present disclosure may be described by the following clauses:

Clause 1. A cardiac atrial retractor ring operable to be flexed between a compressed position having a first circumference and an expanded position having a second circumference, the first circumference being smaller than the second circumference.

Clause 2. The cardiac atrial retractor ring of clause 1, comprising a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment.

Clause 3. The cardiac atrial retractor ring of clause 2, further comprising a plurality of traction points extending outwardly from the plurality of annular segments away from the central point.

Clause 4. The cardiac atrial retractor ring of clauses 2 to 3, wherein an interference between corresponding flexing members prevents the corresponding flexing member from being flexed fully inwardly to the plane.

Clause 5. The cardiac atrial retractor ring of clauses 2 to 4, wherein the corresponding flexing member includes a pair of legs that extend away from the plane when the corresponding flexing member is flexed outwardly away from the central point when the cardiac atrial retractor ring is in the expanded position, and the pair of legs is joined by a foot.

Clause 6. The cardiac atrial retractor ring of clause 5, further comprising a respective traction point extending outwardly from each leg of the pair of legs away from the central point.

Clause 7. The cardiac atrial retractor ring of clauses 5 to 6, wherein a distance between the pair of legs is reduced when the corresponding flexing member flexes inwardly toward the central point and increased when the corresponding flexing member flexes outwardly away from the central point.

Clause 8. The cardiac atrial retractor ring of clauses 5 to 7, wherein the pair of legs are inset toward the central point from the respective annular segment and the adjacent annular segment.

Clause 9. The cardiac atrial retractor ring of clauses 5 to 8, wherein the foot is of a different shape in cross-section than the pair of legs.

Clause 10. The cardiac atrial retractor ring of clauses 5 to 9, wherein the foot comprises an arch that varies in height but not length to move the pair of legs.

Clause 11. The cardiac atrial retractor ring of clauses 1 to 10, wherein an entirety of the cardiac atrial retractor ring is formed from a continuous length of a memory metal wire.

Clause 12. The cardiac atrial retractor ring of clauses 1 to 10, wherein an entirety of the cardiac atrial retractor ring is formed from a continuous length of an elastic plastic material.

Clause 13. The cardiac atrial retractor ring of clauses 1 to 12, wherein a diameter of the cardiac atrial retractor ring is between 20 millimeters and 80 millimeters.

Clause 14. The cardiac atrial retractor ring of clauses 1 to 13, wherein a change between the compressed position and the expanded position is thermally actuated.

Clause 15. A method for retracting an atrium of a heart, comprising: inserting a cardiac atrial retractor ring into the atrium when the cardiac atrial retractor ring is in a compressed position, wherein the cardiac atrial retractor ring is operable to be flexed between the compressed position having a first circumference and an expanded position having a second circumference, the first circumference being smaller than the second circumference; and expanding the cardiac atrial retractor ring into the expanded position, thereby retracting the atrium.

Clause 16. The method of clause 15, wherein the cardiac atrial retractor ring is inserted through a laparoscopic port.

Clause 17. The method of clauses 15 to 16, wherein the cardiac atrial retractor ring expands into the expanded position in response to a change in temperature.

Clause 18. The method of clauses 15 to 17, further comprising engaging striated fibril tissue of the atrium with a plurality of traction points surrounding the cardiac atrial retractor ring.

Clause 19. The method of clauses 15 to 18, further comprising compressing the cardiac atrial retractor ring from the expanded position to the compressed position.

Clause 20. The method of clauses 15 to 19, wherein the cardiac atrial retractor ring comprises a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A cardiac atrial retractor ring operable to be flexed between a compressed position having a first circumference and an expanded position having a second circumference, the first circumference being smaller than the second circumference, the cardiac atrial retractor ring comprising a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment, wherein the corresponding flexing member is composed of a pair of legs that extend away from the plane when the corresponding flexing member is flexed outwardly away from the central point when the cardiac atrial retractor ring is in the expanded position, the pair of legs is inset toward the central point from the respective annular segment and the adjacent annular segment, and the pair of legs is joined by a foot.

2. The cardiac atrial retractor ring of claim 1, further comprising a plurality of traction areas extending outwardly from an outer diameter of the plurality of annular segments away from the central point.

3. The cardiac atrial retractor ring of claim 1, wherein an interference between corresponding flexing members prevents the corresponding flexing member from being flexed fully inwardly to the plane.

4. The cardiac atrial retractor ring of claim 1, wherein a distance between the pair of legs is reduced when the corresponding flexing member flexes inwardly toward the central point and increased when the corresponding flexing member flexes outwardly away from the central point.

5. The cardiac atrial retractor ring of claim 1, wherein the foot is of a different shape in cross-section than the pair of legs.

6. The cardiac atrial retractor ring of claim 1, wherein the foot comprises an arch that varies in height but not length to move the pair of legs.

7. The cardiac atrial retractor ring of claim 1, wherein an entirety of the cardiac atrial retractor ring is formed from a continuous length of a memory metal wire.

8. The cardiac atrial retractor ring of claim 1, wherein an entirety of the cardiac atrial retractor ring is formed from a continuous length of an elastic plastic material.

9. The cardiac atrial retractor ring of claim 1, wherein a diameter of the cardiac atrial retractor ring is between 20 millimeters and 80 millimeters.

10. The cardiac atrial retractor ring of claim 1, wherein a change between the compressed position and the expanded position is thermally actuated.

11. A method for retracting an atrium of a heart, comprising:
inserting a cardiac atrial retractor ring into the atrium when the cardiac atrial retractor ring is in a compressed position, wherein the cardiac atrial retractor ring is operable to be flexed between the compressed position having a first circumference and an expanded position having a second circumference, the first circumference being smaller than the second circumference, wherein the cardiac atrial retractor ring comprises:
a plurality of annular segments arranged circumferentially in a plane about a central point, each respective annular segment of the annular segments being joined to an adjacent annular segment by a corresponding flexing member that is operable to flex inwardly toward the central point to draw the respective annular segment nearer to the adjacent annular segment and to flex outwardly away from the central point to spread the respective annular segment away from the adjacent annular segment, and
wherein the corresponding flexing member includes a pair of legs, the pair of legs is inset toward the central point from the respective annular segment and the adjacent annular segment, and the pair of legs is joined by a foot; and
expanding the cardiac atrial retractor ring into the expanded position, thereby retracting the atrium.

12. The method of claim 11, wherein the cardiac atrial retractor ring is inserted through a laparoscopic port.

13. The method of claim 11, wherein the cardiac atrial retractor ring expands into the expanded position in response to a change in temperature.

14. The method of claim 11, further comprising engaging striated fibril tissue of the atrium with a plurality of traction areas surrounding the cardiac atrial retractor ring.

15. The method of claim 11, further comprising compressing the cardiac atrial retractor ring from the expanded position to the compressed position.

16. The method of claim 11, further comprising reducing a distance between the pair of legs by flexing the corresponding flexing member inwardly toward the central point.

17. The method of claim 11, further comprising increasing a distance between the pair of legs by flexing the corresponding flexing member outwardly away from the central point.

18. The method of claim 11, wherein the foot is of a different shape in cross-section than the pair of legs.

19. The method of claim 11, wherein an entirety of the cardiac atrial retractor ring is formed from a continuous length of a memory metal wire.

20. The method of claim 11, wherein an entirety of the cardiac atrial retractor ring is formed from a continuous length of an elastic plastic material.

\* \* \* \* \*